(12) United States Patent
Holtzapple et al.

(10) Patent No.: US 11,305,086 B2
(45) Date of Patent: *Apr. 19, 2022

(54) AIR-DELIVERY SYSTEM FOR BREATHING-ASSIST DEVICES

(71) Applicant: NozeSeal, LLC, Bryan, TX (US)

(72) Inventors: Mark T. Holtzapple, College Station, TX (US); Lisa Cangelosi Brown, Frisco, TX (US)

(73) Assignee: NozeSeal, LLC, Bryan, TX (US)

(*) Notice: Subject to any disclaimer, the term of this patent is extended or adjusted under 35 U.S.C. 154(b) by 487 days.

This patent is subject to a terminal disclaimer.

(21) Appl. No.: 16/290,707

(22) Filed: Mar. 1, 2019

(65) Prior Publication Data

US 2019/0192803 A1 Jun. 27, 2019

Related U.S. Application Data

(63) Continuation of application No. 13/794,127, filed on Mar. 11, 2013, now Pat. No. 10,238,827.

(60) Provisional application No. 61/609,829, filed on Mar. 12, 2012.

(51) Int. Cl.
*A61M 16/06* (2006.01)
*A61M 16/08* (2006.01)
*A61M 16/04* (2006.01)
*A61M 16/00* (2006.01)

(52) U.S. Cl.
CPC ........ *A61M 16/0666* (2013.01); *A61M 16/06* (2013.01); *A61M 16/0683* (2013.01); *A61M 16/0688* (2014.02); *A61M 16/0069* (2014.02); *A61M 16/049* (2014.02); *A61M 16/0493* (2014.02); *A61M 16/0633* (2014.02); *A61M 16/0875* (2013.01); *A61M 2205/8206* (2013.01); *A61M 2205/8212* (2013.01); *A61M 2210/0625* (2013.01)

(58) Field of Classification Search
CPC .......... A61M 16/0666; A61M 16/0688; A61M 16/0685; A61M 16/06; A61M 16/087; A61M 2205/0226; A61M 25/02; A61J 15/0053
See application file for complete search history.

(56) References Cited

U.S. PATENT DOCUMENTS

| | | |
|---|---|---|
| 612,997 A | 10/1898 | Smith |
| 5,025,805 A | 6/1991 | Nutter |
| 6,328,038 B1 | 12/2001 | Kessler et al. |

(Continued)

OTHER PUBLICATIONS

International Search Report dated Sep. 27, 2013 in connection with International Patent Application No. PCT/US2013/30535, 5 pages.

(Continued)

*Primary Examiner* — Margaret M Luarca

(57) ABSTRACT

An embodiment of the disclosure provides a universal sealing apparatus for one or more cannulas. The apparatus includes a first portion, a second portion, and a third portion. The first and second portions are configured to removably adhere directly or indirectly to a nose. The third portion is coupled to the first and second portions. The third portion removably couples to one or more cannulas and places a force upon a base of flared portions of the one or more cannulas when the first and second portions are adhered to the nose. The force maintains a fluid seal of the one or more cannulas within one or more respective nostrils of the nose.

21 Claims, 23 Drawing Sheets

(56) References Cited

U.S. PATENT DOCUMENTS

| | | |
|---|---|---|
| 6,669,712 B1 | 12/2003 | Cardoso |
| 6,675,796 B2 | 1/2004 | McDonald |
| 7,024,235 B2 | 4/2006 | Melker et al. |
| 7,331,348 B1 | 2/2008 | Beevers |
| 7,353,826 B2 | 4/2008 | Sleeper et al. |
| 7,658,189 B2 | 2/2010 | Davidson et al. |
| 2004/0211430 A1 | 10/2004 | Pivovarov |
| 2004/0226566 A1 | 11/2004 | Gunaratnam et al. |
| 2004/0230108 A1 | 11/2004 | Melker et al. |
| 2005/0092329 A1 | 5/2005 | Sta-Maria |
| 2005/0103347 A1 | 5/2005 | Curti et al. |
| 2005/0268914 A1 | 12/2005 | Paoluccio et al. |
| 2008/0041373 A1 | 2/2008 | Doshi |
| 2008/0060657 A1 | 3/2008 | McAuley et al. |
| 2008/0190436 A1 | 8/2008 | Jaffe et al. |
| 2009/0101147 A1 | 4/2009 | Landis et al. |
| 2009/0241961 A1 | 10/2009 | McAuley et al. |
| 2009/0250066 A1 | 10/2009 | Daly |
| 2009/0275851 A1 | 11/2009 | Colman et al. |
| 2010/0000534 A1 | 1/2010 | Kooij et al. |
| 2010/0132717 A1 | 6/2010 | Davidson et al. |
| 2011/0067704 A1 | 3/2011 | Kooij et al. |
| 2012/0138060 A1 | 6/2012 | Barlow |
| 2012/0234323 A1 | 9/2012 | Connor |
| 2012/0318270 A1 | 12/2012 | McAuley et al. |
| 2013/0092173 A1 | 4/2013 | Alexander et al. |
| 2013/0118498 A1 | 5/2013 | Robitaille et al. |

OTHER PUBLICATIONS

Written Opinion of International Searching Authority dated Sep. 27, 2013 in connection with International Patent Application No. PCT/US2012/30535, 7 pages.

Partial Supplementary European Search Report dated Jun. 16, 2015 in connection with European Application No. 13760934.3, 5 pages.

Supplementary European Search Report dated Oct. 22, 2015 in connection with European Patent Application No. EP 13 76 0934, 9 pages.

FIGS. 1A, 1B, and 1C: Embodiment 1V

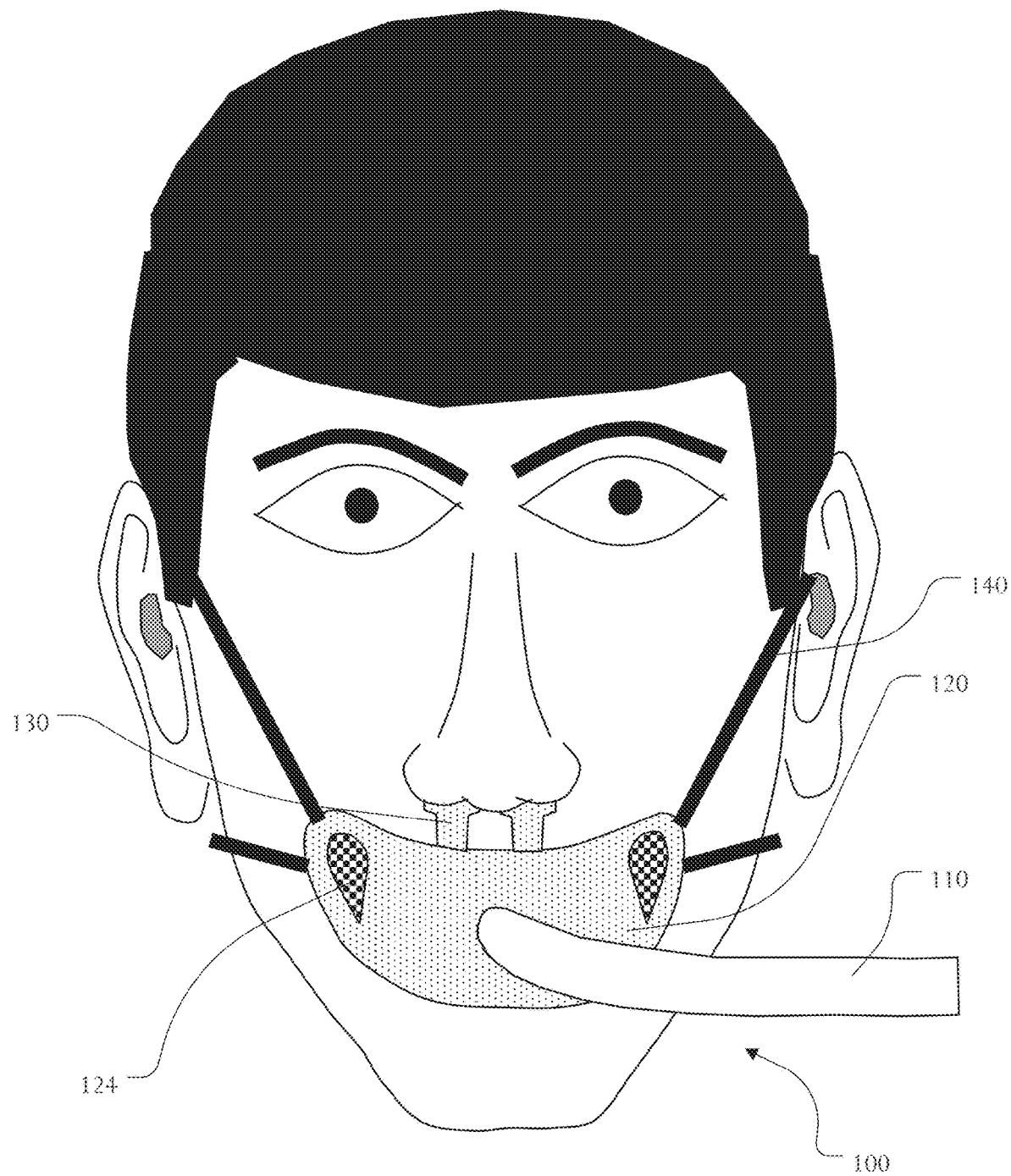
FIG. 2: Embodiment IV

FIGS. 3A, 3B, and 3C: Embodiment 1R

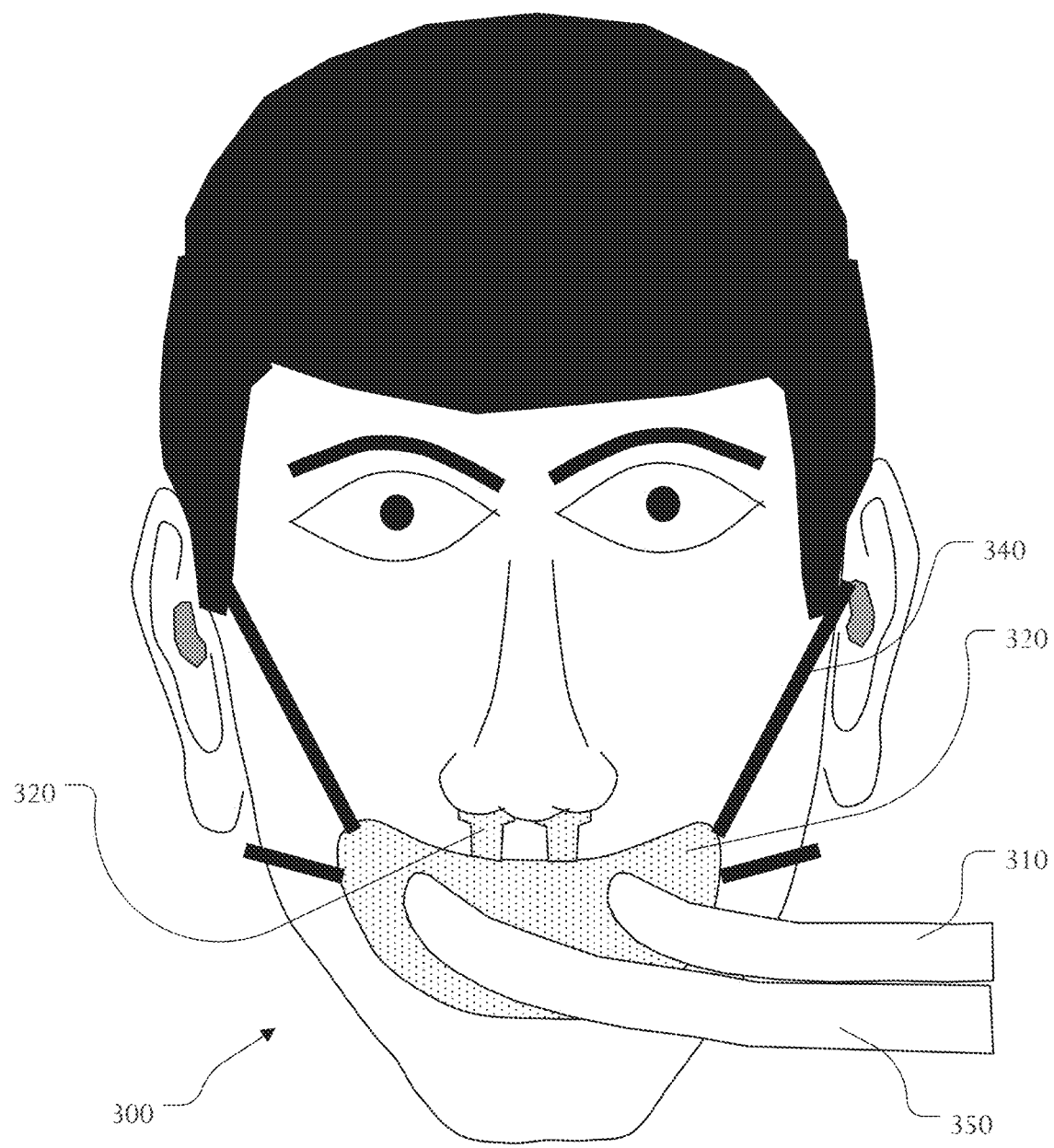
FIG. 4: Embodiment 1R

FIGS. 5A, 5B, and 5C: Embodiment 2V

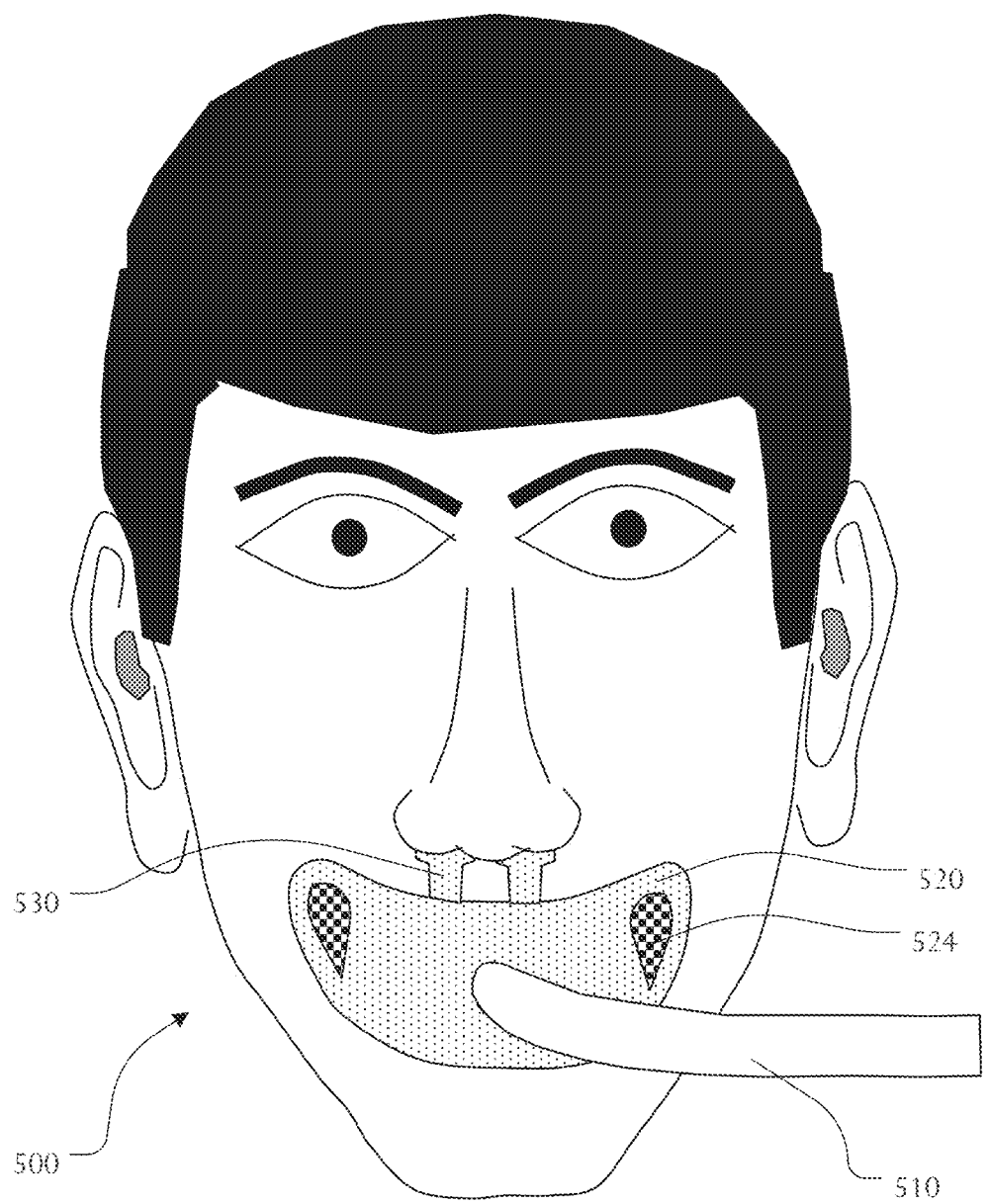
FIG. 6: Embodiment 2V

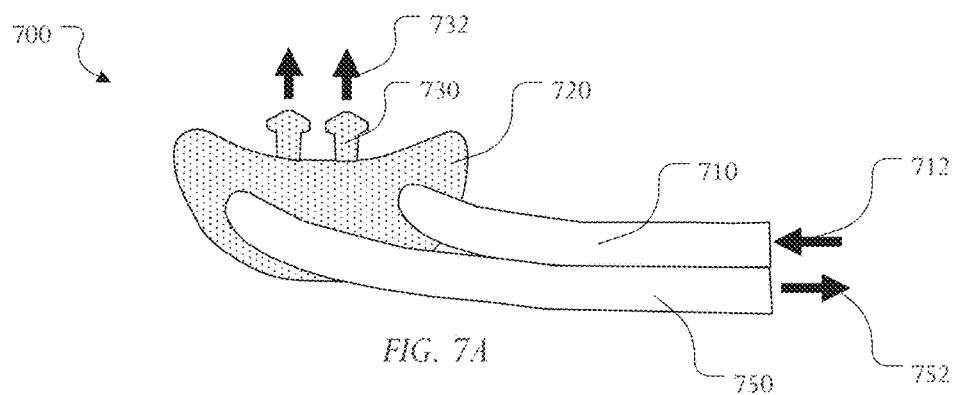
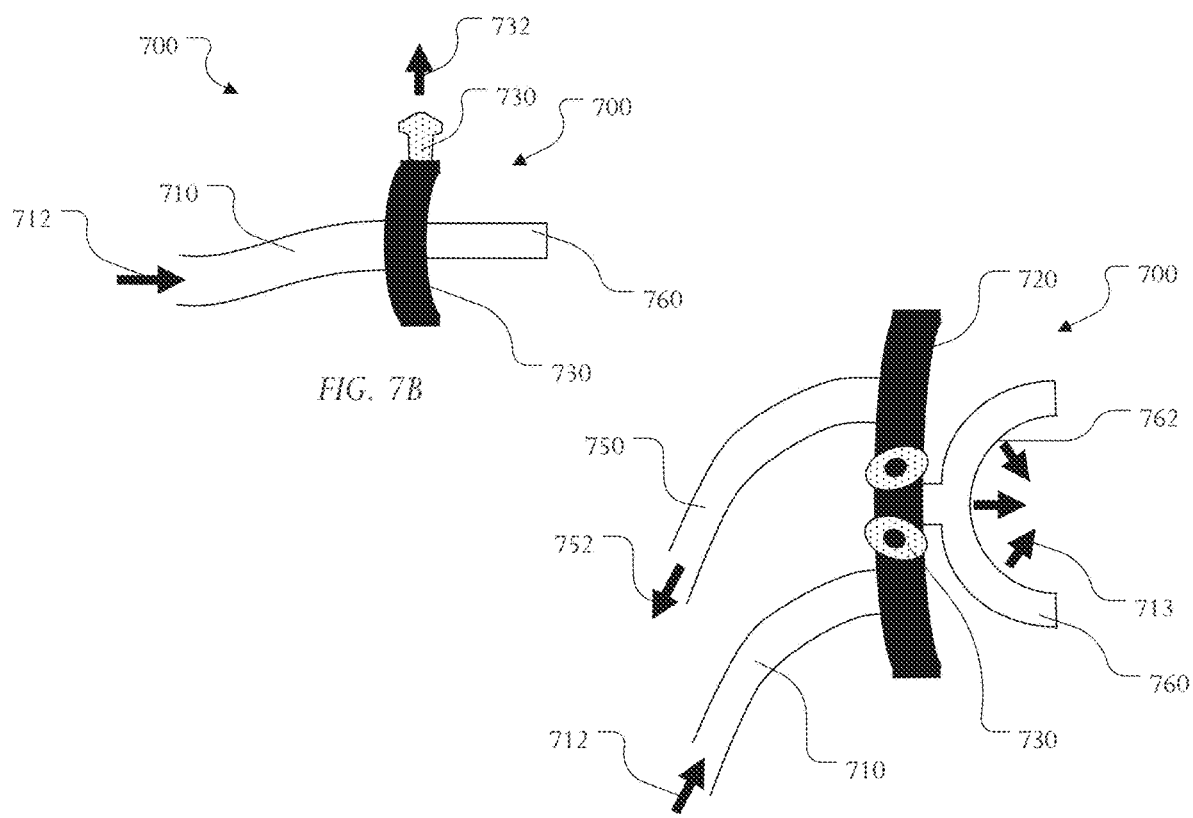
FIGS 7A, 7B, and 7C: Embodiment 2R

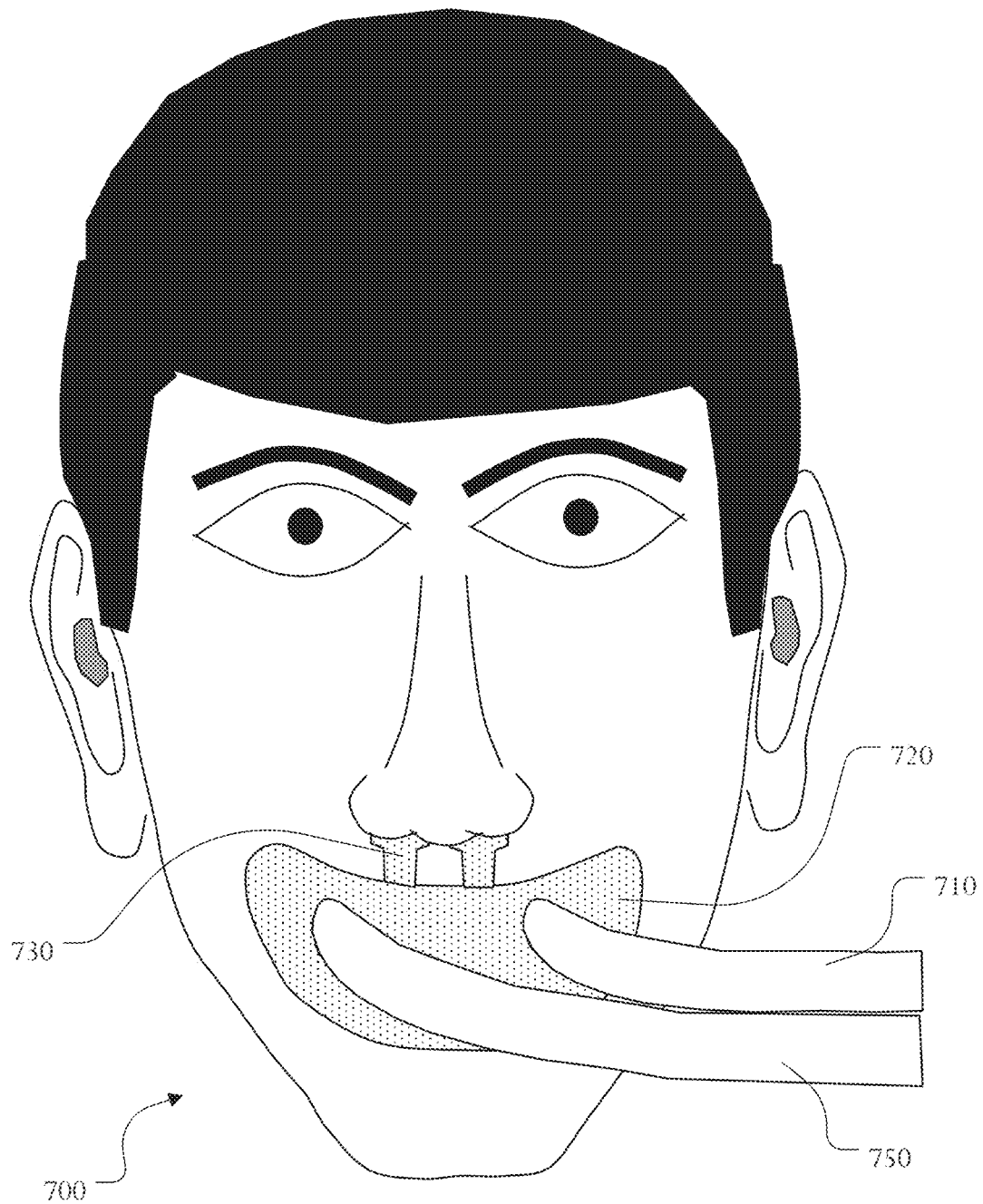
FIG. 8: Embodiment 2R

FIGS. 9A and 9B: Embodiment 3V

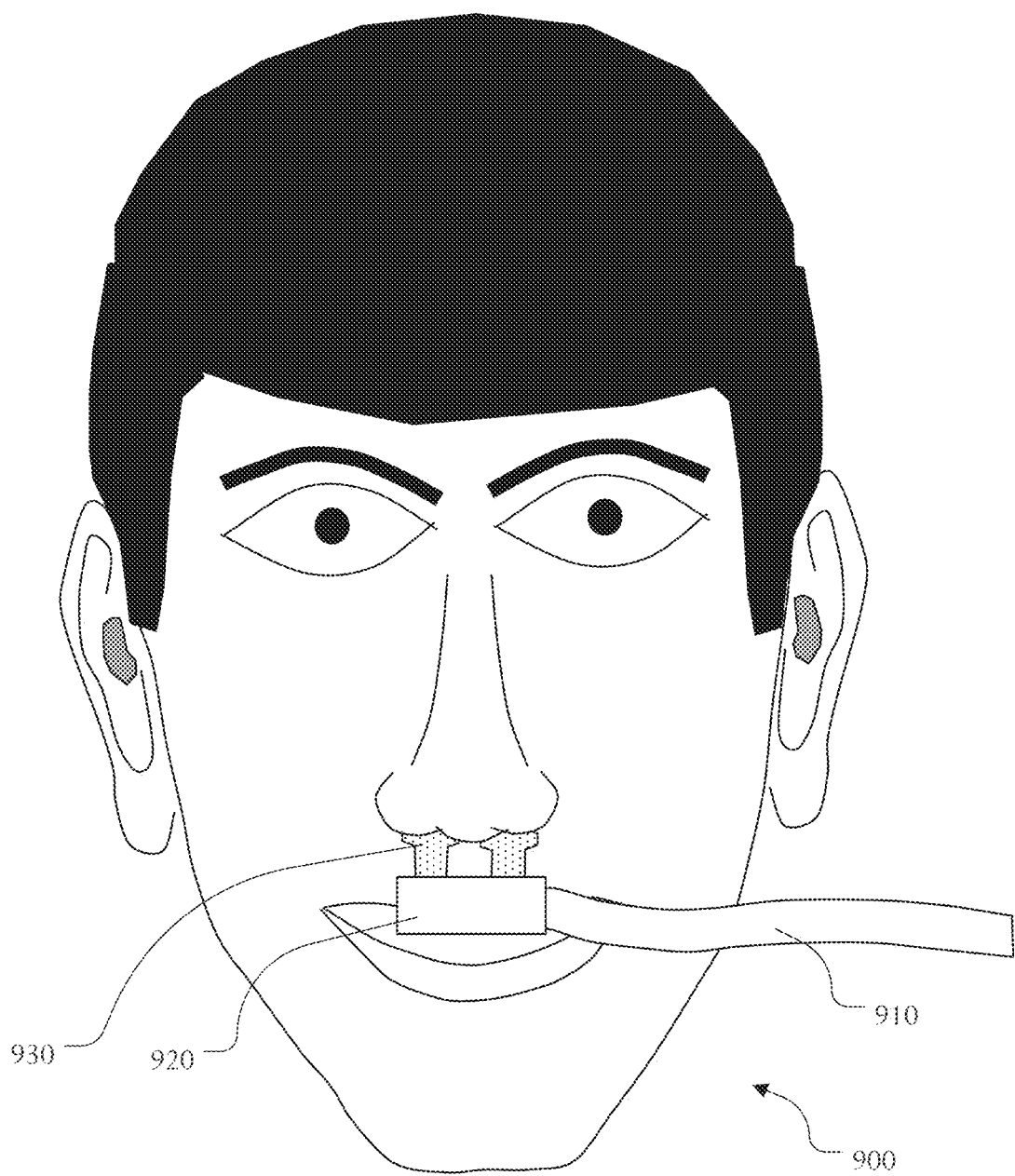
FIG. 10: Embodiment 3V

FIGS.11A and 11B: Embodiment 3R

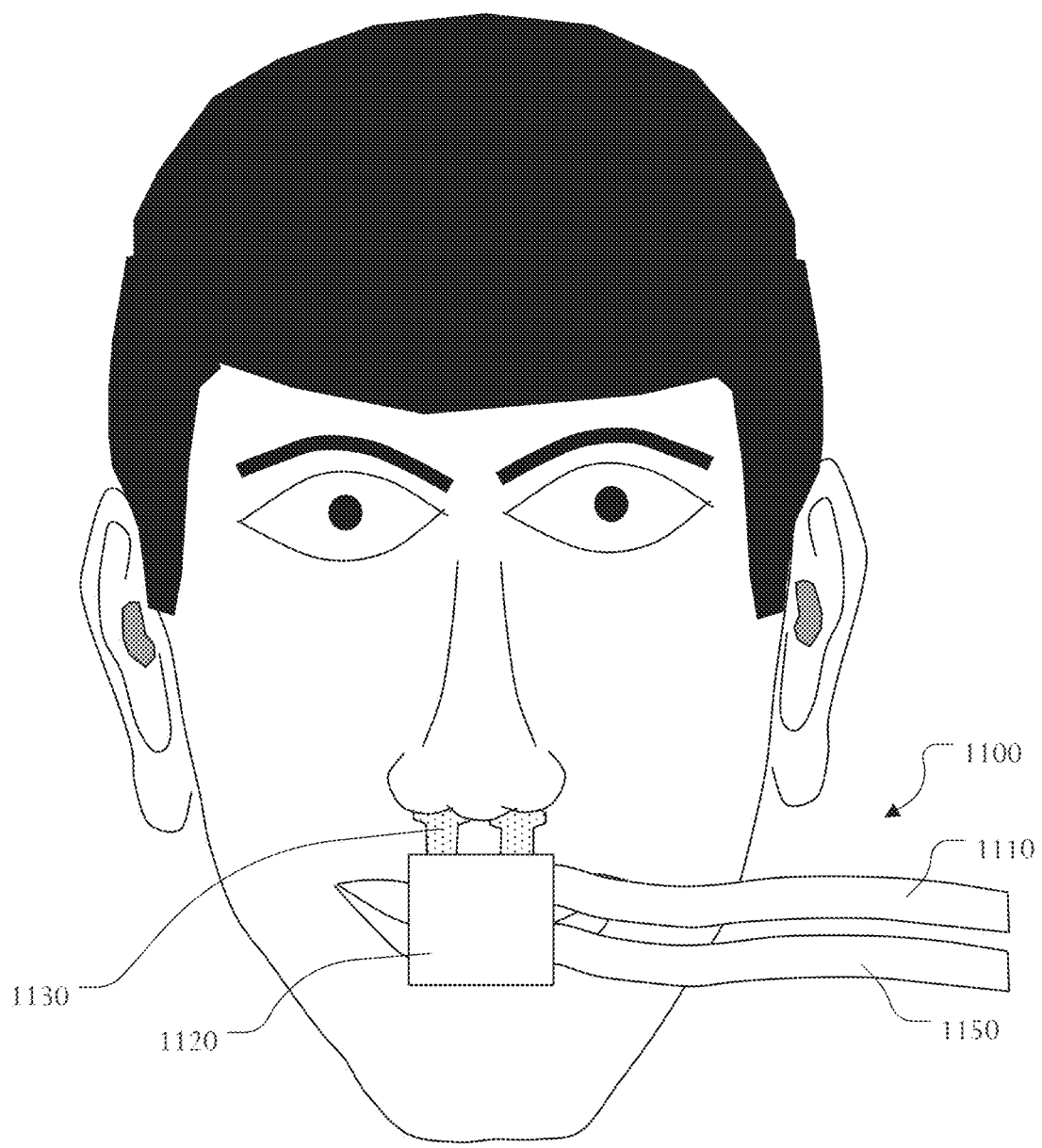
FIG. 12: Embodiment 3R

FIGS. 13A, 13B, and 13C: Embodiment A

FIGS. 14A and 14B: Embodiment B

FIGS. 15A and 15B: Embodiment C

AIR-DELIVERY SYSTEM FOR BREATHING-ASSIST DEVICES

CROSS-REFERENCE TO RELATED APPLICATIONS AND CLAIM OF PRIORITY

This application is a continuation of U.S. patent application Ser. No. 13/794,127 filed on Mar. 11, 2013, which claims priority under 35 U.S.C. § 119(e) to U.S. Provisional Patent Application No. 61/609,829 filed on Mar. 12, 2012. Both of these applications are hereby incorporated by reference in their entirety.

TECHNICAL FIELD

The present disclosure is directed, in general, to breathing-assist systems, and more specifically, to an air-delivery system for breathing-assist devices.

SUMMARY

An embodiment of the disclosure provides a universal sealing apparatus for one or more cannulas. The apparatus includes a first portion, a second portion, and a third portion. The first and second portions are configured to removably adhere directly or indirectly to a nose. The third portion is coupled to the first and second portions. The third portion removably couples to one or more cannulas and places a force upon a base of flared portions of the one or more cannulas when the first and second portions are adhered to the nose. The force maintains a fluid seal of the one or more cannulas within one or more respective nostrils of the nose.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 2 shows the installation of the air-delivery system of FIGS. 1A, 1B, and 1C;

FIG. 4 shows the installation of the air-delivery system of FIGS. 3A, 3B, and 3C;

FIG. 6 shows the installation of the air-delivery system of FIGS. 5A, 5B, and 5C;

FIGS. 7A, 7B, and 7C show three views of an air-delivery system, according to another embodiment of the disclosure;

FIG. 8 shows the installation of the air-delivery system of FIGS. 7A, 7B, and 7C;

FIG. 10 shows the installation of the air-delivery system of FIGS. 9A and 9B;

FIG. 12 shows the installation of the air-delivery system of FIGS. 11A and 11B;

DETAILED DESCRIPTION

The FIGURES, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system. Additionally, the drawings are not necessarily drawn to scale.

Contextually, embodiments of the disclosure are directed towards an air-delivery system that provides pressurized air to patients with breathing problems. A typical application of the air-delivery system is as a Continuous Positive Airway Pressure (CPAP) device, which is used to address sleep apnea and snoring.

The majority of conventional CPAP air-delivery systems employ face masks that must be strapped to the head, which is uncomfortable. These systems employ a mask that covers both the mouth and nose, which is difficult to seal properly.

Some air-delivery systems employ a cannula that is inserted into the nose; however, it is difficult to seal the cannula resulting in air leaks that disturb sleep. Additionally, as described in more detail below, such cannula sealing systems require special components that are specific to the manufacturer of such components. They are not universal; thus, one purchasing components from one manufacturer must return to the same manufacture for replacement parts.

A commercially available "no-mask" air-delivery system uses teeth to mechanically support a cannula inserted into the nose. Unfortunately, this system delivers air only to the nose and not the mouth, which makes breathing difficult if the nose is blocked by a cold, for example. A further disadvantage is that using teeth to support the air-delivery system makes it difficult to talk.

Given these difficulties, certain embodiments of the disclosure provide a system that addresses some or all of the difficulties discussed above. Certain embodiments may have one or more of the following unique features:
  A cannula sealing system to prevent air leakage from the nose, which reduces noise and provides better sleep;
  A universal sealing apparatus that can be used with virtually any manufacturer's cannula;
  A pressure recovery system that reduces energy consumption, which reduces noise and makes the system more suitable for portable operation under battery power;
  A strap-free air-delivery system that provides air to both the nose and mouth; and
  A strap-free air-delivery system that provides air to the nose only and requires no mechanical support from the teeth.

Although the above unique features are specifically identified, other unique features may also become apparent after review of the disclosure. Additionally, some of embodiments may have none of the above-list of unique features.

Air-Delivery System

Figure 1A:
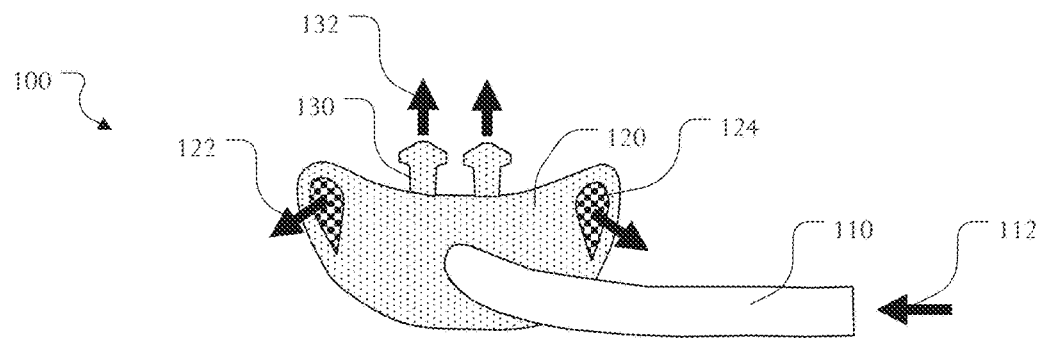
FIGS. 1A, 1B, and 1C show three views of an air-delivery system, according to an embodiment of the disclosure.
Figure 1B:
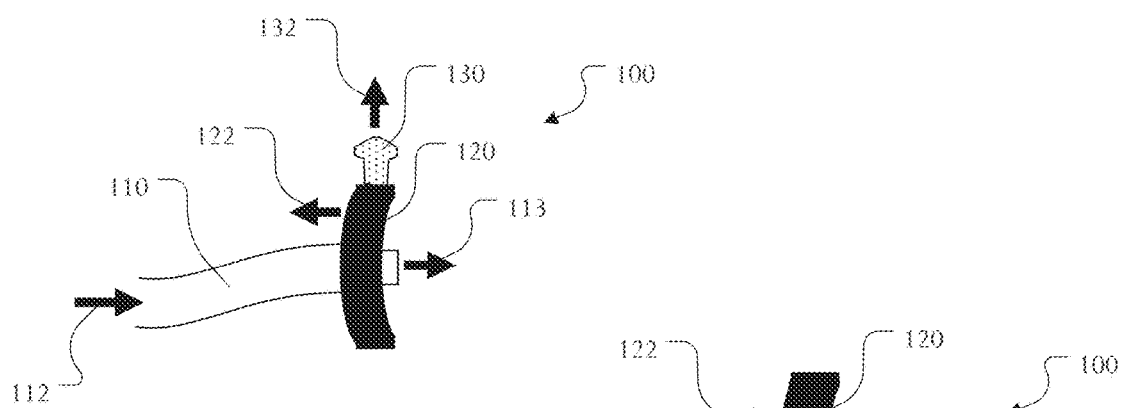
Figure 1C:
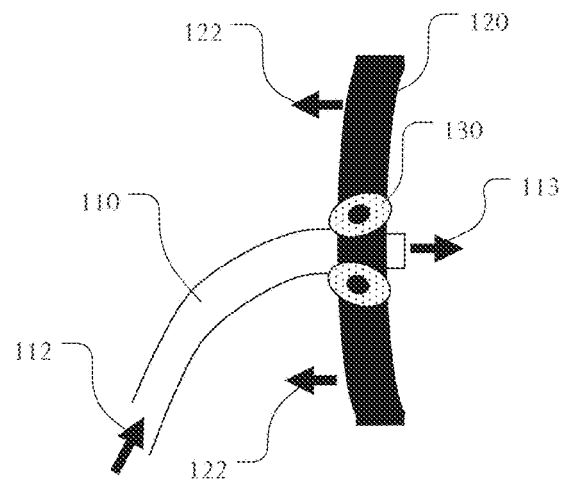

FIGS. 1A, 1B, and 1C show three views of an air-delivery system 100, according to an embodiment of the disclosure. FIG. 1A is a front view, FIG. 1B is a side view, and FIG. 1C is a top view. These three FIGURES have been annotated with "Embodiment 1V" where V stands for "vent." Embodiment 1V features a single hose 110 that delivers pressurized air (indicated by arrows 112) to a hollow mouth seal 120, which distributes air (indicated by arrows 113 and 132) to the mouth and nose via two cannulas 130. Exhaust gas (indicated by arrow 122) is vented from the mouth seal 120 through exhaust ports 124.

FIG. 2 shows the installation of the air-delivery system 100 of FIGS. 1A, 1B, and 1C. In this particular embodiment, one or more straps 140 are used to secure the air-delivery system 100. However, other securing mechanisms may also be used, for example, as described with reference to other FIGURES below.

Figure 3A:
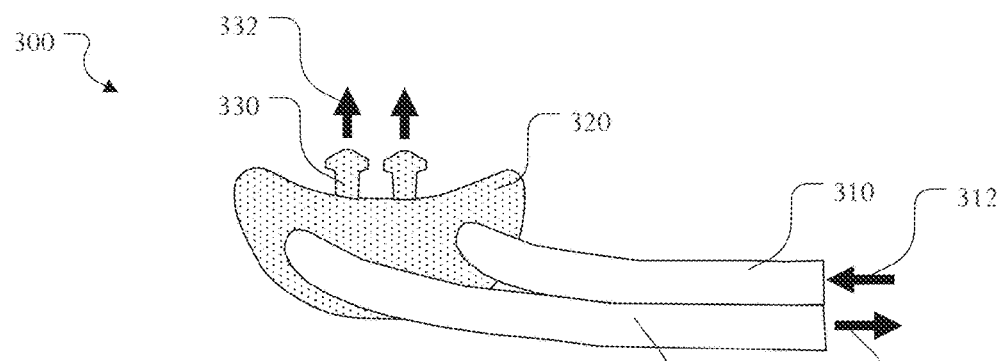
FIGS. 3A, 3B, and 3C show three views of an air-delivery system, according to another embodiment of the disclosure.
Figure 3B:
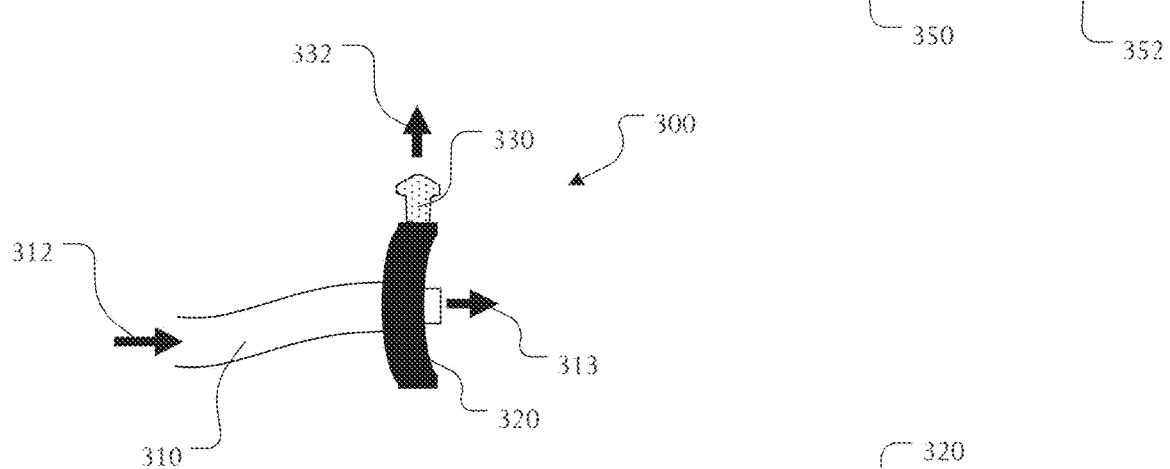
Figure 3C:
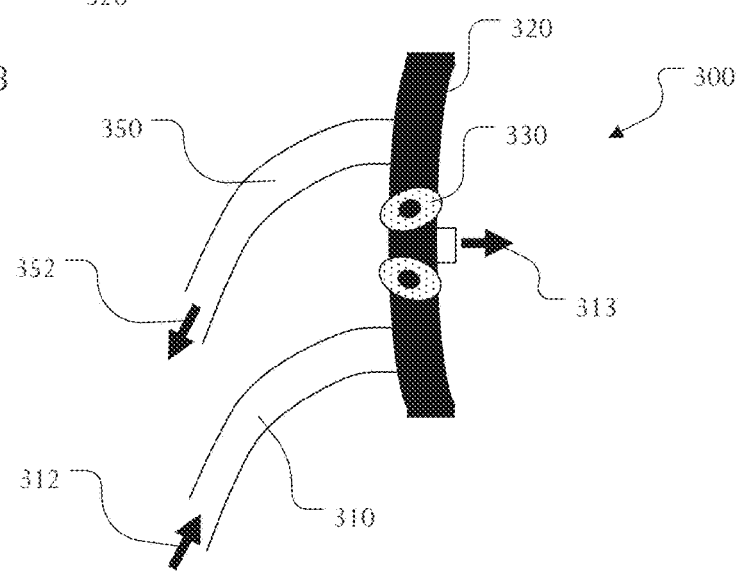

FIGS. 3A, 3B, and 3C show three views of an air-delivery system 300, according to another embodiment of the disclosure. FIG. 3A is a front view, FIG. 3B is a side view, and FIG. 3C is a top view. These three FIGURES have been annotated with "Embodiment 1R" where R stands for pressure "recovery." Embodiment 1R is nearly identical to Embodiment 1V of FIGS. 1A, 1B, 1C, and 2, for example, including an input hose 310 that delivers pressured arrow (indicated by arrow 312) to the hollow mouth seal 320, which distributes air (indicated by arrows 313 and 332) to the mouth and nose via two cannulas 330. However, FIGS. 3A, 3B, and 3C also include a second hose 350 that directs vented gas (indicated by arrow 352) away from the air-delivery system 300.

FIG. 4 shows the installation of the air-delivery system 300 of FIGS. 3A, 3B, and 3C. In this particular embodiment, straps 340 are used to secure the air-delivery system. However, other securing mechanisms may also be used, for example, as described with reference to other FIGURES below.

Figure 5A:
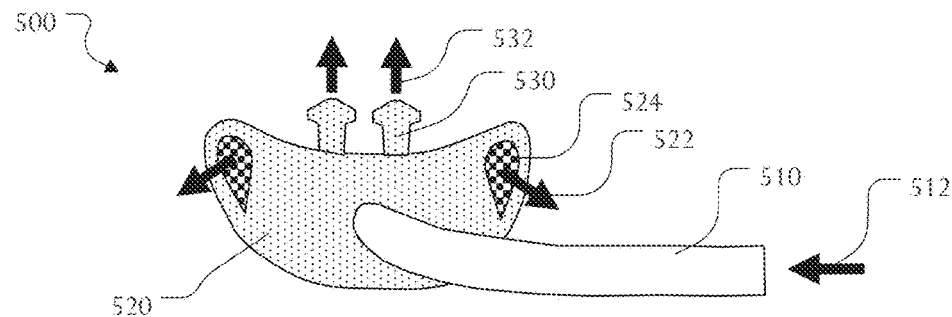
FIGS. 5A, 5B, and 5C show three views of an air-delivery system, according to another embodiment of the disclosure.
Figure 5B:
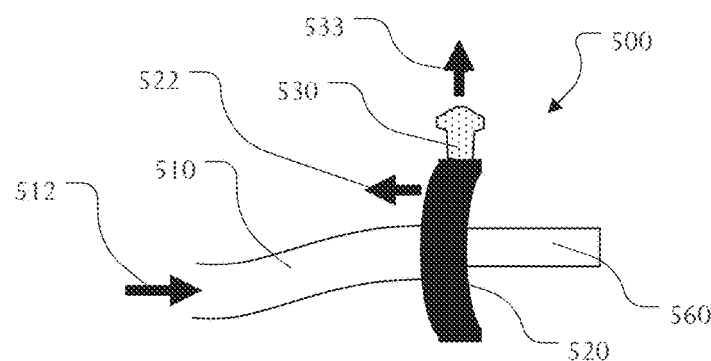
Figure 5C:
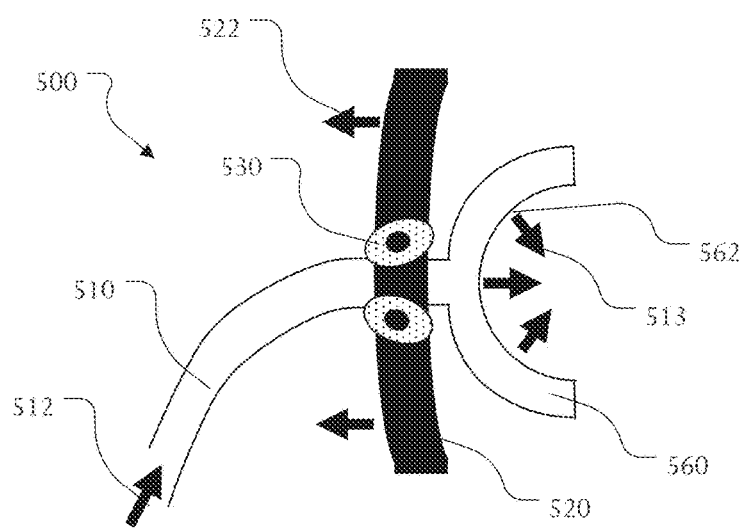

FIGS. 5A, 5B, and 5C show three views of an air-delivery system 500, according to another embodiment of the disclosure. FIG. 5A is a front view, FIG. 5B is a side view, and FIG. 5C is a top view. These three FIGURES have been annotated with "Embodiment 2V" where V, again, stands for "vent." Embodiment 2V features a single hose 510 that delivers pressurized air (indicated by arrows 512) to the hollow mouth seal 520, which distributes air (indicated by arrows 513 and 532) to the mouth and nose via two cannulas 530. Exhaust gas (indicated by arrow 522) is vented from the mouth seal 520 through exhaust ports 524. This embodiment features a mouth guard 560, which is clamped between the teeth to provide mechanical support. Passageways 562 in the mouth guard 560 allow air delivery to the mouth.

The mouth guard 560 (any other mouth guards described herein) may be configured in any suitable manner. For example, in one particular configuration, the passageways 562 are made of a material that is non-deformable by heat or thermal energy. However, certain portion of the mouth guard 560 may be deformable with heat, for example, upon placing the mouth guard 560 in boiling water. Thus, a user of the mouth guard 560 may have the guard shaped to his or her teeth upon "biting" the heated deformable portions—in a similar manner to a football mouth guard. Upon cooling, a customized mouth guard is produced. Any suitable gap may be used to ensure air flow into the mouth.

Unlike conventional mouth guards, certain configurations simultaneously provide air to both the mouth and the nose—thus alleviating problems that may occur when a user has a clogged nose.

FIG. 6 shows the installation of the air-delivery system 500 of FIGS. 5A, 5B, and 5C. In this particular embodiment, no straps are required because the mouth guard (not seen in this view) mechanically secures the air-delivery system 500.

FIGS. 7A, 7B, and 7C show three views of an air-delivery system 700, according to another embodiment of the disclosure. FIG. 7A is a front view, FIG. 7B is a side view, and FIG. 7C is a top view. These three FIGURES have been annotated with "Embodiment 2R" where R, again, stands for pressure "recovery." Embodiment 2R is nearly identical to Embodiment 2V of FIGS. 5A, 5B, 5C, and 6, for example, including an input hose 710 that delivers pressured arrow (indicated by arrow 712) to the hollow mouth seal 720, which distributes air (indicated by arrows 713 and 732) to the mouth and nose via two cannulas 730. Additionally, the air-delivery system 700 includes a mouth guard 760 with passageways 762. However, FIGS. 7A, 7B, and 7C also include a second hose 750 that directs vented gas (indicated by arrow 752) away from the air-delivery system 700. By directing vented gas away from a user, hissing noises that are typically encountered in CPAP configurations may be alleviated or completely avoided.

FIG. 8 shows the installation of the air-delivery system 700 of FIGS. 7A, 7B, and 7C. In this particular embodiment, no straps are required because the mouth guard mechanically secures the air-delivery system 700.

Figure 9A:
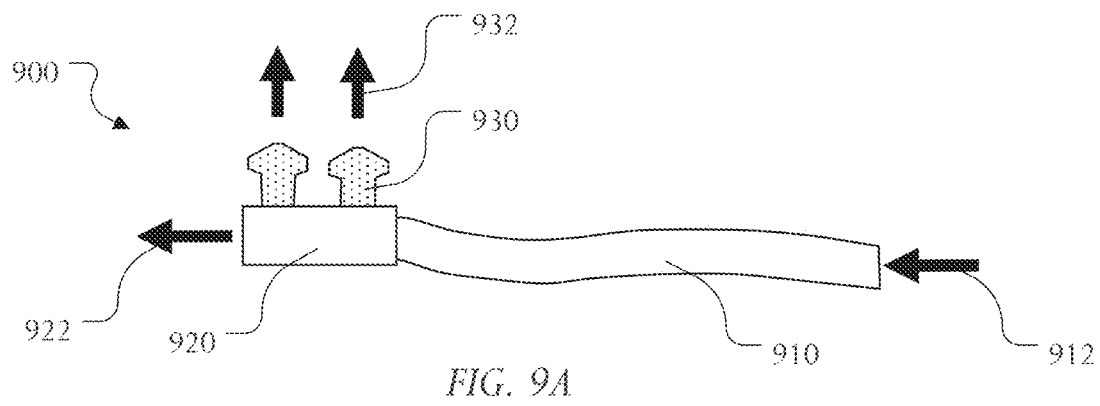
FIGS. 9A and 9B show two views of an air-delivery system, according to another embodiment of the disclosure.
Figure 9B:
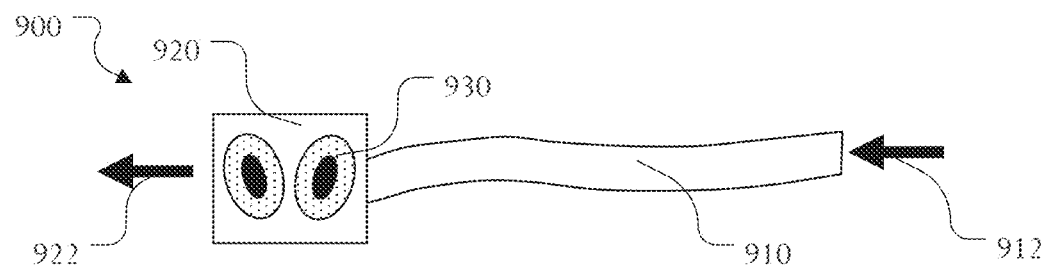

FIGS. 9A and 9B show two views of an air-delivery system 900, according to another embodiment of the disclosure. FIG. 9A is a front view and FIG. 9B is a side view. These two FIGURES have been annotated with "Embodiment 3V" where V, again, stands for "vent." Embodiment 3V features a single hose 910 that delivers pressurized air (indicated by arrows 912) to a cannula distributor 920, which distributes air (indicated by arrows 932) to the nose through two cannulas 930. Exhaust air is vented (as indicated by arrow 922) from the cannula distributor 920.

FIG. 10 shows the installation of the air-delivery system 900 of FIGS. 9A and 9B.

Figure 11A:
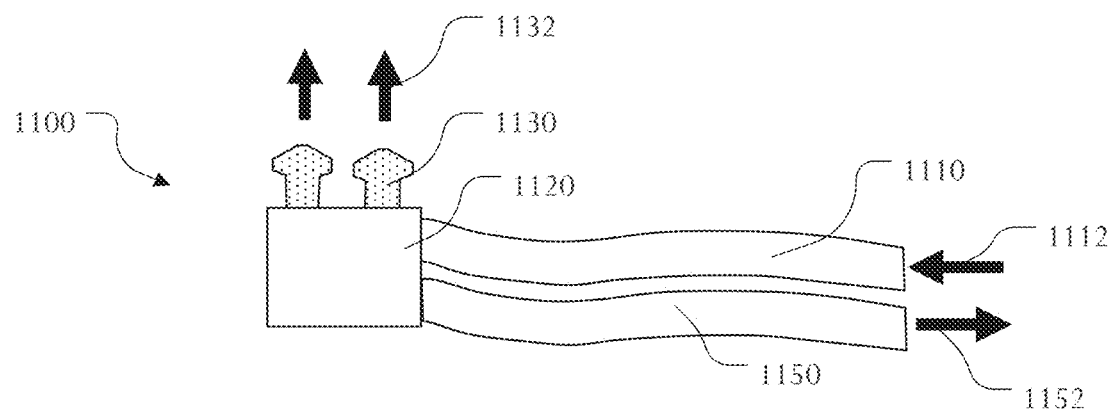
FIGS. 11A and 11B show two views of an air-delivery system, according to another embodiment of the disclosure.
Figure 11B:
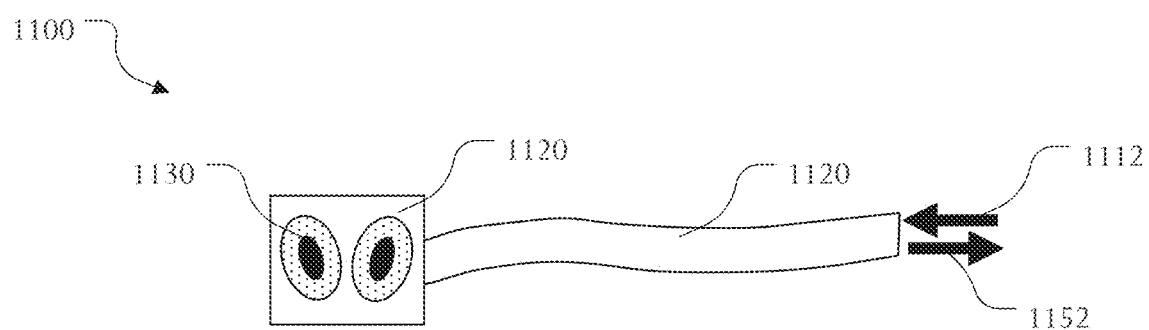

FIGS. 11A and 11B show two views of an air-delivery system 1100, according to another embodiment of the disclosure. FIG. 11A is a front view and FIG. 11B is a side view. These two FIGURES have been annotated with "Embodiment 3R" where R, again, stands for pressure "recovery." Embodiment 3R is nearly identical to Embodiment 3V of FIGS. 9A, 9B, 9C, and 10, for example, including an input hose 1110 that delivers pressurized air (indicated by arrows 1112) to a cannula distributor 1120, which distributes air (indicated by arrows 1132) to the nose through two cannulas 1130. However, FIGS. 11A and 11B also include a second hose 1150 that directs vented gas away (indicated by arrow 1152) from the air-delivery system 1100.

FIG. 12 shows the installation of the air-delivery system 1100 of FIGS. 11A and 11B.

Cannula Seals

As described above, some air-delivery systems insert a cannula (sometimes described as a nose pillow) within a nostril of a nose. Several examples are described in U.S. Pat. No. 8,291,906, assigned to ResMed. To affix the mask to the face, this patent describes the use of adhesive strips that replace straps, which are traditionally used. Because these adhesive strips are uniquely designed to interface with a given mask, the components from one manufacturer are not interchangeable with those of another. In other words, they are not universal. Thus, a user of components from one CPAP manufacturer must continue to purchase components from the same CPAP manufacturer.

The adhesive strips described in U.S. Pat. No. 8,291,906—which are used to affix the mask to the face—do not necessarily result in an effective seal of the cannula to the nostril. If the user bumps the mask—which readily occurs during sleep—then the cannulas can become dislodged from the nostril, resulting in a noisy leak that can awaken the user. This ineffective seal results because the adhesive strips do not interface directly with the cannula. Rather, the adhesive strips attach directly to the face mask, which in turn mechanically couples to the cannulas. Accordingly, the force for the cannula seal is transported from the adhesive connection mechanism, to the mask, and then to the cannulas or pillows. Such an indirect configuration inhibits the ability for an effective seal.

Recognizing such problems, certain embodiments of the disclosure provide a universal cannula sealing mechanism that can be used with virtually any manufacture's cannula or nose pillow. Moreover, in contrast to attaching adhesive strips to the mask, certain embodiments of the disclosure attach adhesive strips directly to a cannula or pillow—thus, ensuring a better seal.

Figure 13A:
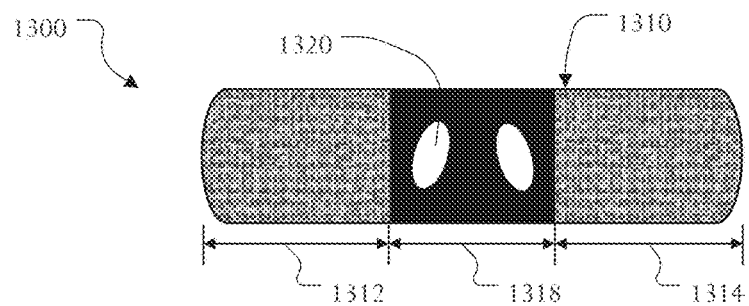
FIGS. 13A, 13B, and 13C show three views of one cannula-sealing apparatus, according to an embodiment of the disclosure.
Figure 13B:
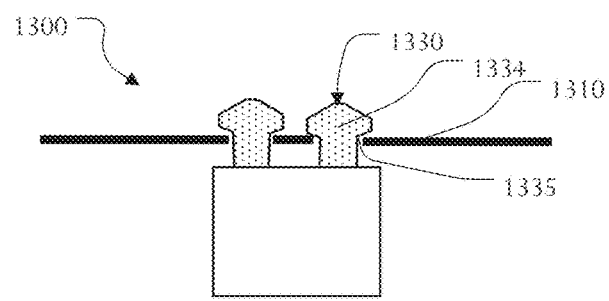
Figure 13C:
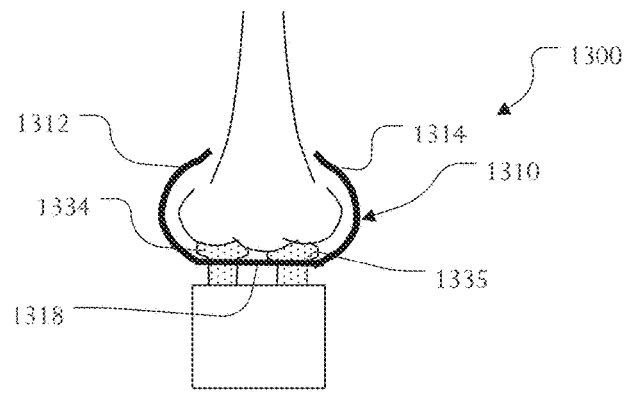

FIGS. 13A, 13B, and 13C show three views of one cannula-sealing apparatus 1300, according to an embodiment of the disclosure. FIG. 13A is a top view, FIG. 13B is a side view, and FIG. 13C is a side view of the installation. These three FIGURES have been annotated with "Embodiment A."

The cannula-sealing apparatus 1300 in FIGS. 13A, 13B, and 13C generally shows a continuous member 1310 with two holes 1320 placed therein for the receiving of cannulas 1330. The continuous member 1310 may be made from virtually any material or combinations of materials, including, but not limited to, fabric, latex rubber, or plastics such as polyvinyl chloride or polyethylene. Yet other materials will become apparent to one of ordinary skill in the art after review of the present disclosure.

The continuous member 1310 in this configuration is shown as having portions 1312, 1314, and 1318. Portions 1312 and 1314 generally correspond to adhering portions of the continuous member 1310. Such portions have any structure that allows the continuous member 1310 to directly or indirectly adhere to a nose as shown in FIG. 13C. In the particular configurations, the adhering portions may include an adhesive on a least one side. Further, in particular configurations, the adhesive on portions 1312 and 1314 may be pressure sensitive, allowing the portions 1312 and 1314 to adhere to the skin when pressed. The adhesive may be any of a variety of suitable materials including, but not limited to, rubbers, acrylate, and silicone formulations.

Portion 1318, which is shown with the holes 1320, is generally configured to operate directly with a flared portion 1334 of the cannula 1330 as seen in FIG. 13B. In particular, as seen in FIG. 13B, portion 1318 comes into contact with a base 1335 of the flared portion 1334. When the cannulas 1330 are placed in the nostrils of the nose as shown in FIG. 13C, a user may pull and adhere portions 1312 and 1314 to respective side of the nose. In particular configuration, the continuous member 1310 may have at least a partial flexible "give" because of the materials utilized. In other configurations, the continuous member 1310 may have little or no give. This action forces portion 1318 to press upward upon the base 1335 of the flared portion 1334 of the cannula 1330 to keep the cannulas 1330 sealingly engaged in their respective nostrils. As a user of the cannula-sealing apparatus 1300 sleeps, for example, the upward force of portion 1318 keeps the sealing engagement of the cannula 1330 within the respective nostril.

The holes 1320 in portion 1318 are configured such that the cannulas 1330 are allowed to be positioned therethrough. Then, after the positioning of the cannulas 1330 therethrough, the holes 1320 do not allow an easy unintentional extraction of the cannulas 1330. In the particular configuration shown, the holes 1320 have an oval shape that allows passage of the flared portion 1334 of the cannula 1330, which is flexible. The flared portion 1334 of the cannula 1330 will not readily pass back through such holes 1320 unless intentionally forced by the user. One of ordinary skill in the art will recognize such a design after review of this disclosure. Although such a particular design is shown for the holes 1320 in this configuration, others designs will become apparent to one of ordinary skill in the art after review of the present disclosure.

In particular configurations, the portion 1318 may have or be made of a different material than portions 1312 and 1314. For example, in particular configurations, the portion 1318 may lack an adhesive. In particular configurations, the portion 1318 may be reinforced—having extra material as may be necessary. In particular configurations, the reinforcement may be around the holes 1320 using materials, such as, but not limited to, polyester resin marketed as MYLAR®, cellulose acetate, cellophane, polyethylene, or polypropylene.

In particular embodiments, the cannula-sealing apparatus 1300 of FIGS. 13A, 13B, and 13C can be seen as a universal sealing system for air-delivery systems that have cannulas. In particular, because the sealing system interacts directly with the flared portion 1334 (namely, the base 1335) of the cannula 1330, virtually any air-delivery system with cannulas may avail from embodiments of the disclosure—without modification.

In particular configurations, the cannula-sealing apparatus 1300 may be used as long as the adhesive on portions 1312 and 1314 retain their properties. In particular configurations, the cannula-sealing apparatus 1300 is discardable after use. Particular advantages of this embodiment may include a low-tech configuration that may be relatively easy to manufacture.

Although the cannula-sealing apparatus 1300 has been described as having an adhesive portion and being disposable, the adhering portions of the cannula-sealing apparatus may have other configurations. As one non-limiting example, a disposable strip may be placed across the bridge and down the sides of a nose. Then, the adhering portions of the cannular seal may adhere to the nose indirectly through the disposable strip using, for example, hook and loop fasteners or adhesive on both the adhering portion of the seal and the disposable strip. In particular embodiments, the disposable strip may be a strip configured to keep the nostrils open such as those marketed under the trade name BREATHE RIGHT® nasal strips. In such configurations, a user may apply the nasal strips, insert the cannulas, and then attach the portion 1312 and 1314 to the nasal strips.

Figure 14A:
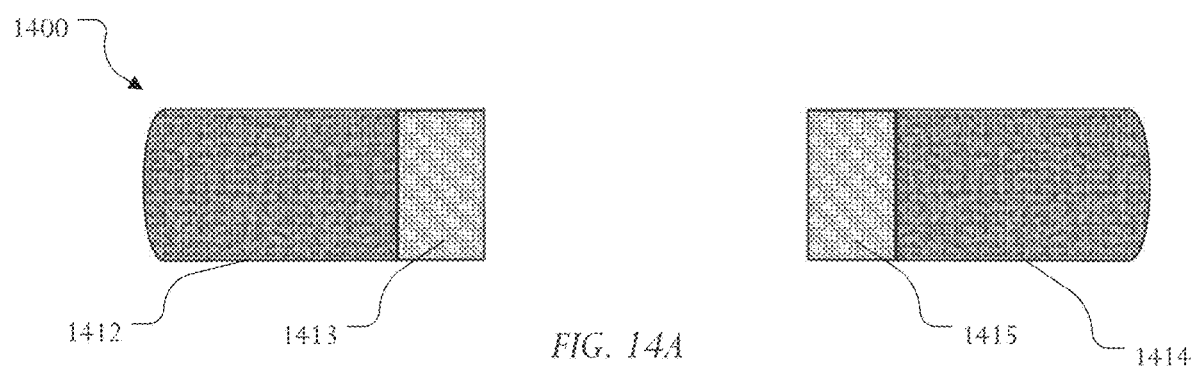
FIGS. 14A and 14B show two views of another cannula-sealing apparatus, according to an embodiment of the disclosure.
Figure 14B:
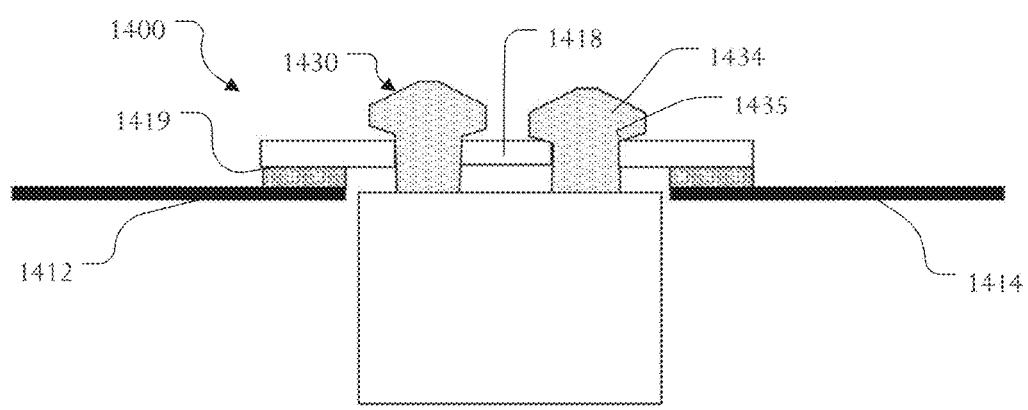
Figure 15A:
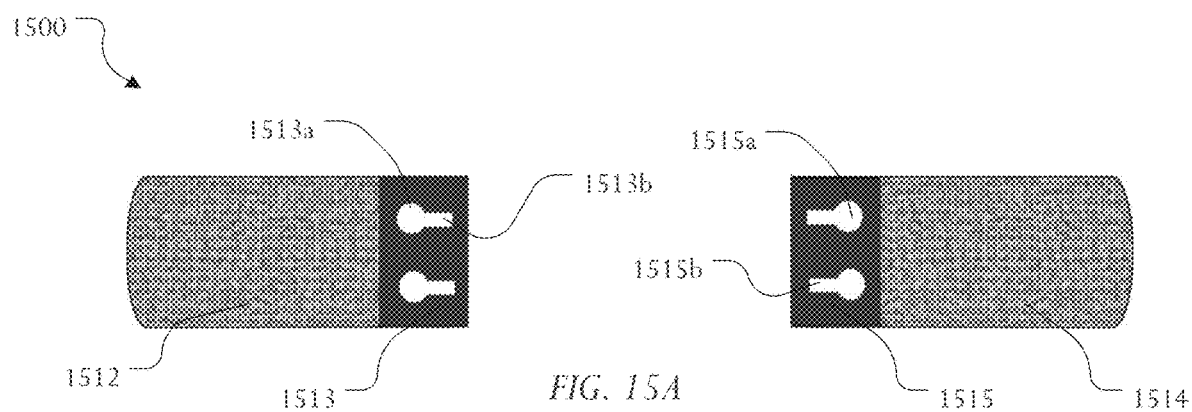
FIGS. 15A and 15B show two views of another cannula-sealing apparatus, according to an embodiment of the disclosure.
Figure 15B:
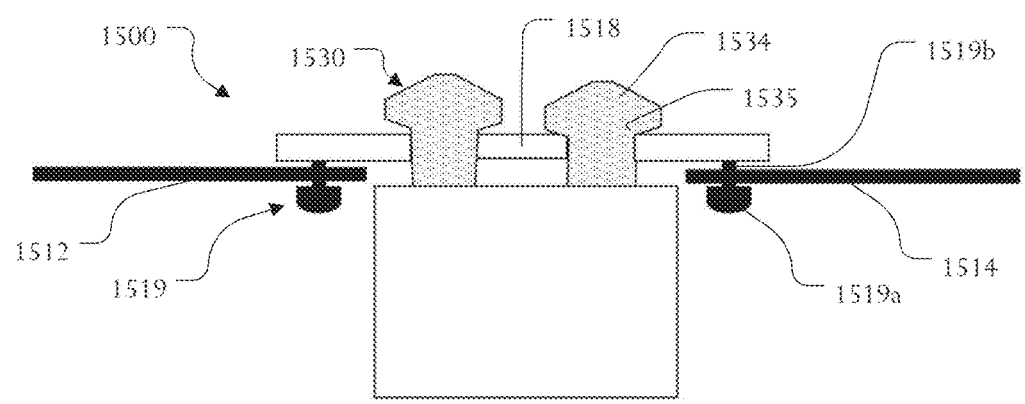

FIGS. 14A, 14B, 15A, and 15B show non-limiting examples of embodiments in which a cannula-sealing apparatus is not continuous and has portions that are removable from other portions. FIGS. 14A and 14B show one example of removability of portions whereas FIGS. 15A and 15B show another example of removability of portions. It should be understood that such examples are non-limiting as others will become apparent to one of ordinary skill in the art after having read the present disclosure.

FIGS. 14A and 14B show two views of a cannula-sealing apparatus, according to an embodiment of the disclosure. FIG. 14A is a top view and FIG. 14B is a side view. These two FIGURES have been annotated with "Embodiment B."

Similar to FIGS. 13A, 13B, and 13C, the cannula-sealing apparatus 1400 of FIGS. 14A and 14B include multiple portions 1412 and 1414 that are configured to adhere directly or indirectly to a nose and another portion 1418 that interacts with the cannula 1430. However, portions 1412 and 1414 are removable from portion 1418. To enable this removability, either or both of the removable portions (1412, 1414) and portion 1418 include a sticky material such as hook-and-loop fasteners (commonly marketed under the name VELCRO®). These features have respectively been labeled as connectors 1413, 1415, and 1419. The operation of such materials should become apparent to one of ordinary skill in the art after review of this disclosure.

Because of the removability of portions 1412 and 1414, portion 1418 may exhibit qualities different than portion 1318 of FIGS. 13A, 13B, and 13C. For example, portions 1412 and 1414 may only be disposable, allowing one to only have to push the cannulas through holes in portion 1418 once. Additionally, a higher quality more expensive material may be chosen for portion 1418.

Once the portions 1412 and 1414 are coupled to portion 1418, the cannula-sealing apparatus 1400 may operate in the same manner as the cannula-sealing apparatus 1300 with respect to sealing placement of the cannulas in the nostrils, including attachment of the portions to the nose.

FIGS. 15A and 15B show two views of a cannula-sealing apparatus, according to another embodiment of the disclosure. FIG. 15A is a top view and FIG. 15B is a side view. These two FIGURES have been annotated with "Embodiment C."

Similar to FIGS. 14A and 14B, the cannula-sealing apparatus 1500 of FIGS. 15A and 15B include multiple portions 1512 and 1514 that are configured to adhere directly or indirectly to a nose and another portion 1518 that interacts with the cannula 1530. Additionally, similar to FIGS. 14A and 14B, FIGS. 15A and 15B, portions 1512 and 1514 are removable from portion 1518, and to enable this removability, either or both of the removable portions (1512, 1514) and portion 1518 include connectors 1513, 1515, and 1519. However, the connectors 1513, 1515, and 1519 of FIGS. 15A and 15B are different than the connectors 1413, 1415, and 1419 of FIGS. 14A and 14B. In particular, connectors 1513, 1515 include respective holes 1513*a*, 1515*a*, and grooves 1513*b*, 1515*b*. Additionally, connector 1519 has a knob 1519*a* with a thinner stem 1519*b*. The holes 1513*a*, 1515*a* receive the knob 1519*a* and the stem 1519*b* passes along the grooves 1513*b*, 1515*b*. Then, the knob 1519*a* is prevented from being pulled through the grooves 1513*b*, 1515*b*. Such an operation will become apparent to one of ordinary skill in the art having read this disclosure.

Once the portions 1512 and 1514 are coupled to portion 1518, the cannula-sealing apparatus 1500 may operate in the same manner as the cannula-sealing apparatus 1300 with respect to sealing placement of the cannulas in the nostril and the portions on the nose.

As referenced above, FIGS. 14A, 14B, 15A, and 15B show non-limiting examples of embodiments in which a cannula-sealing apparatus is not continuous and has portions that are removable from other portions. Other manners of connecting portions may also be utilized according to embodiments. As one non-limiting example, portions may be belted to one another using any suitable technique. As another limiting example, a portion may include a connector that is allowed to pass through another respective connector in only one direction. Such technology is similar to those used in retail outlets for tagging clothing with prices. In such configurations, the only way to remove the connector is to tear the connector. Yet other connection mechanisms will become apparent to one of ordinary skill in the art having read the disclosure.

Figure 16:
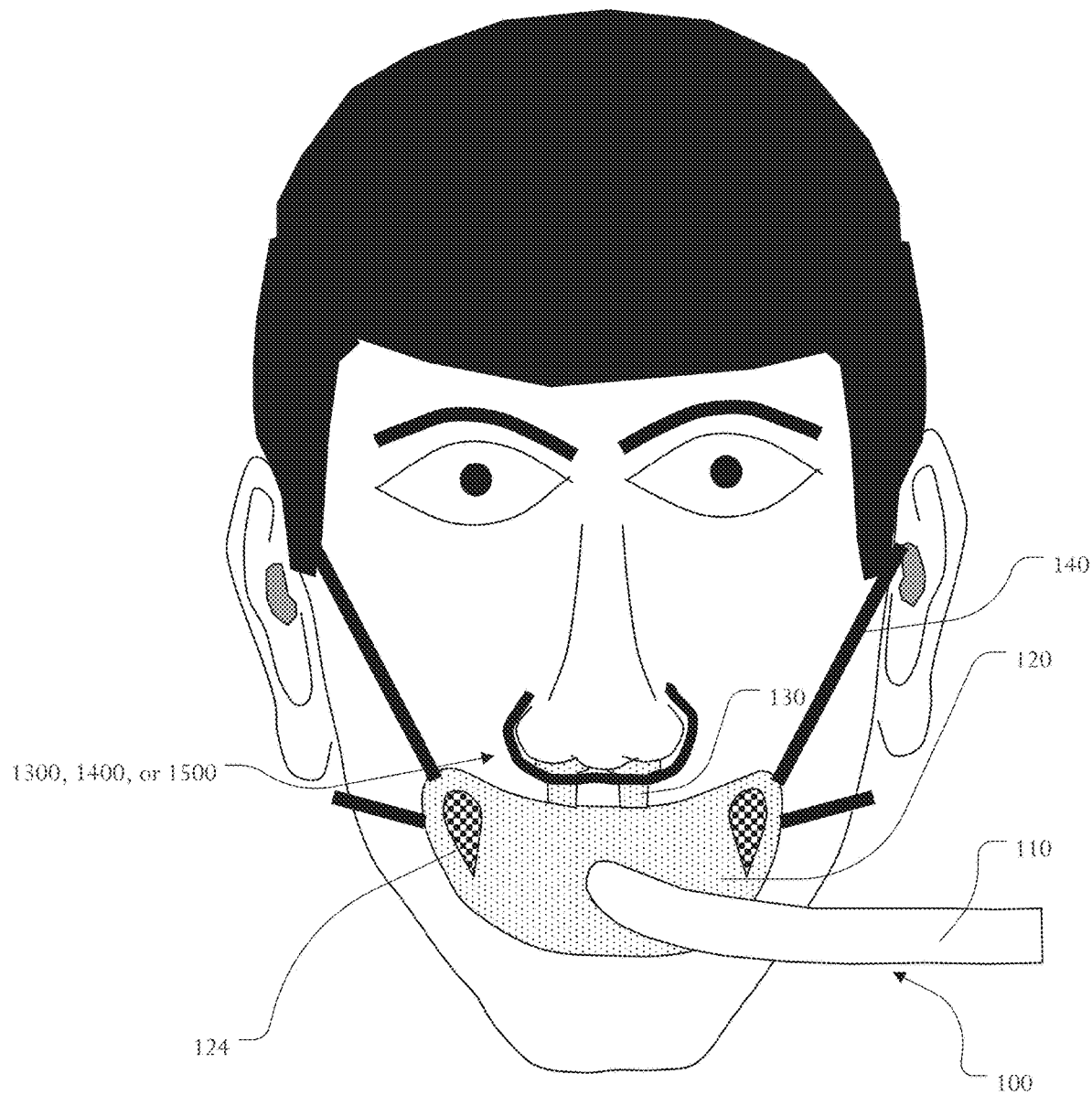
FIG. 16 shows the air-delivery system of FIGS. 3A, 3B, 3C, and 4 with an installed cannula-sealing apparatus.
Figure 17:
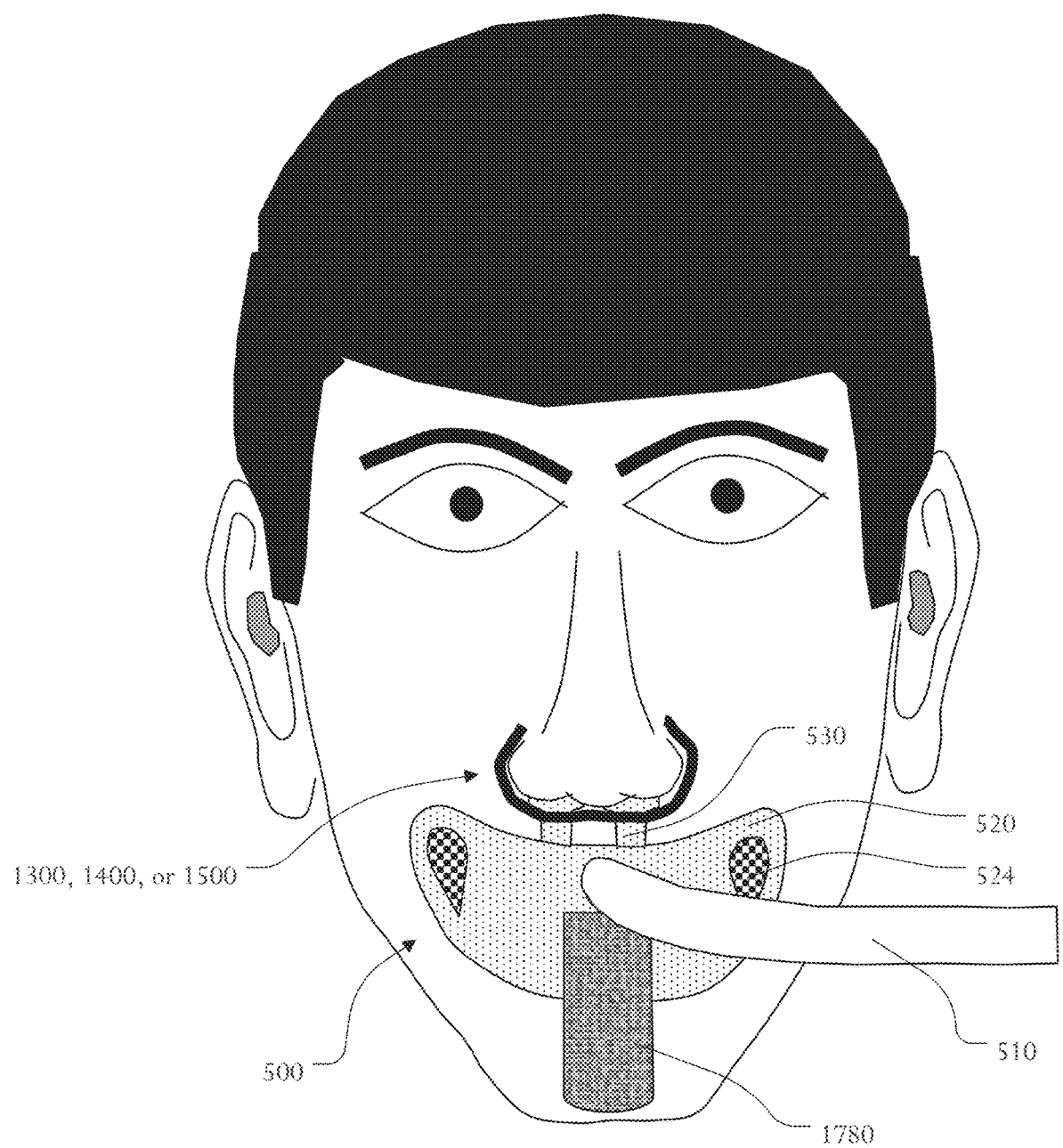
FIG. 17 shows the air-delivery system of FIGS. 5A, 5B, 5C, and 6 with an installed cannula-sealing apparatus.
Figure 18:
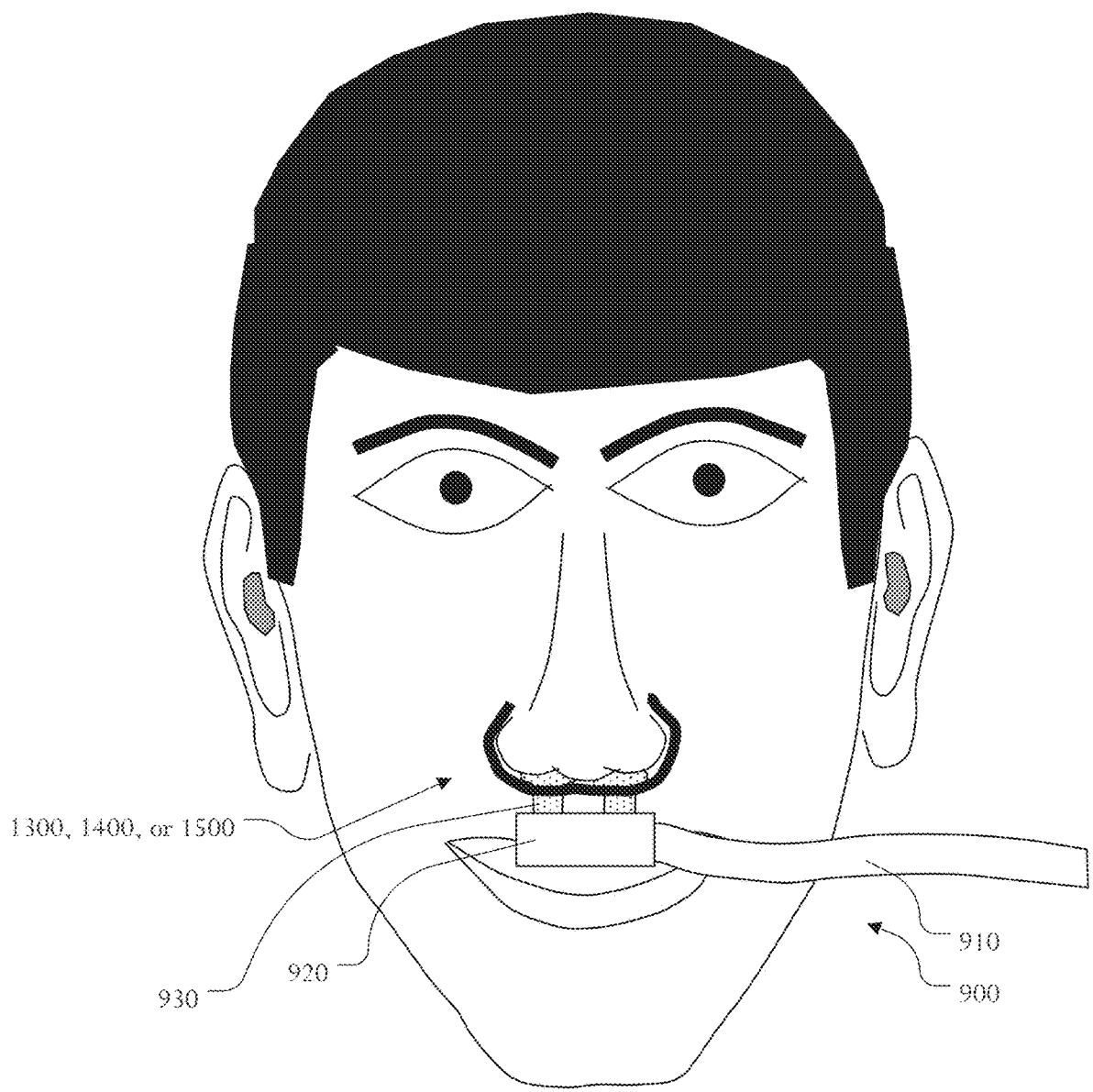
FIG. 18 shows the air-delivery system of FIGS. 9A, 9B, and 10 with an installed cannula-sealing apparatus.

FIGS. 16, 17, and 18 show how various different configurations disclosed herein can be combined. Although the specific combination will be shown, other combinations may also be utilized according to embodiments of the disclosure.

FIG. 16 shows the air-delivery system of Embodiment 1V with installed cannula-sealing apparatus (Embodiment A, B, or C). Although Embodiment 1V is shown here, Embodiment 1R could be employed as well in this configuration.

FIG. 17 shows the air-delivery system Embodiment 2V with installed cannula-sealing apparatus (Embodiment A, B, or C). Optionally, chin tape 1780 can be used to ensure that the mouth stays closed. Although Embodiment 2V is shown here, Embodiment 2R could be employed as well in this configuration.

FIG. 18 shows the air-delivery system Embodiment 3V with an installed cannula-sealing apparatus (Embodiment A, B, or C). Although Embodiment 3V is shown here, Embodiment 3R could be employed as well in this configuration.

Figures 19A, 19B:
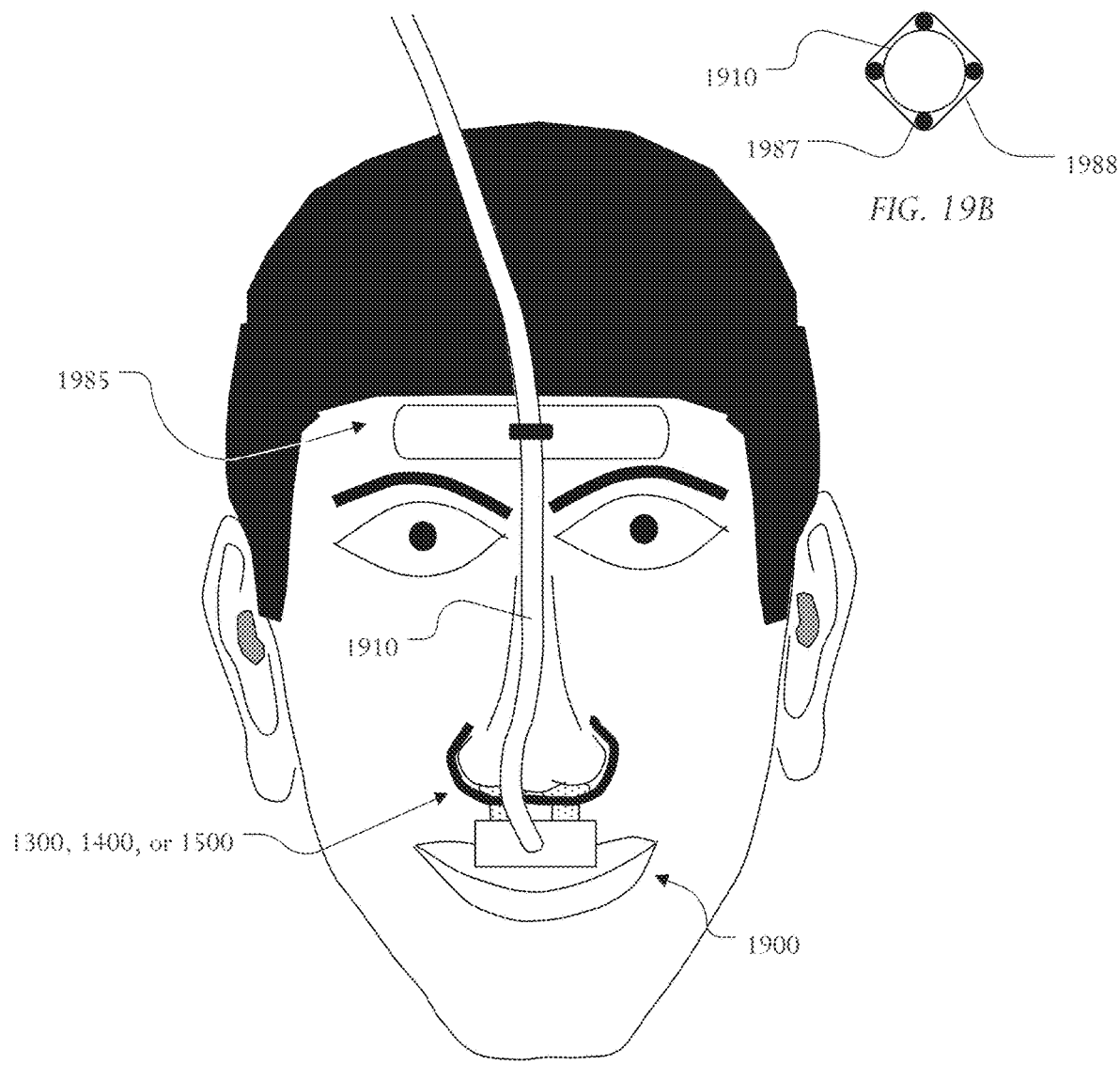
FIGS. 19A and 19B show a configuration of an air-delivery system with an installed cannula-sealing apparatus plus support structure secured to the forehead using double-stick tape.

FIG. 19A shows a configuration of an air-delivery system 1900 with an installed cannula-sealing apparatus (Embodiment A, B, or C). The air-delivery system 1900 may operate in a substantially similar to the air-delivery system 900 of FIGS. 9A, 9B, and 10. This embodiment also includes a support structure 1985 that secures to the forehead using, for example, double-stick tape. In an alternative configuration, suction cups may be used. In particular configurations, as shown in cross-sectional detail of FIG. 19B, the flexible hose 1910 can be surrounded with wire 1987 and a wrap 1988 so that it can be bent to a shape that fits the face comfortably. These two FIGURES have been annotated with "Embodiment 4V," where "V," again stands for vent. Although Embodiment 4V is shown here, a similar Embodiment 4R (where "R," again stands for pressure "recovery") could be employed as well in this configuration.

Figures 20A, 20B:
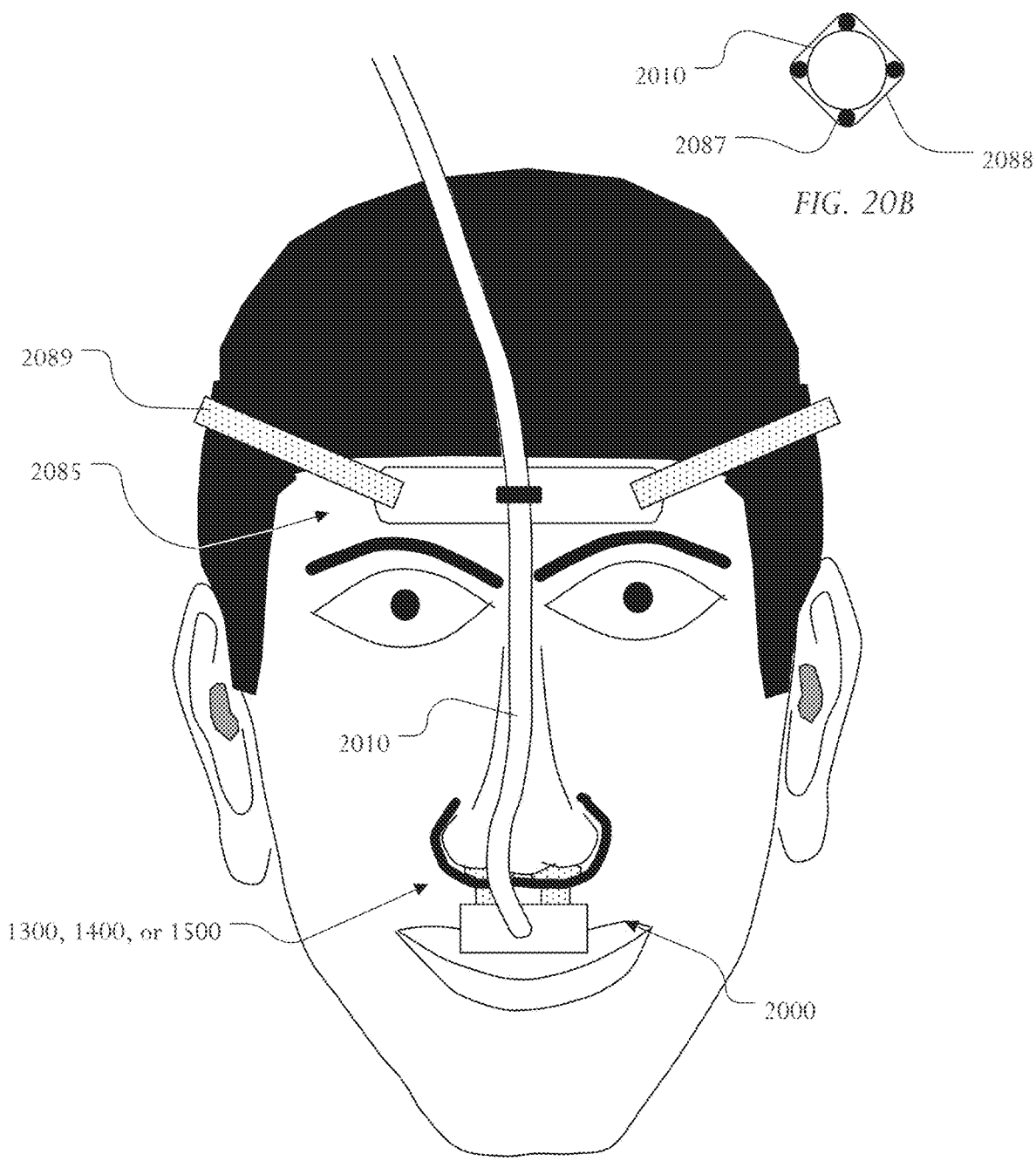
FIGS. 20A and 20B show a configuration of an air-delivery system with an installed cannula sealing apparatus plus support structure secured to the forehead using straps.

FIG. 20A shows a configuration of an air-delivery system 2000 with installed cannula-sealing apparatus (Embodiment A, B, or C). The air-delivery system 2000 may operate in a substantially similar to the air-delivery system 900 of FIGS. 9A, 9B, and 10. This embodiment also includes a support structure 2085 secured to the forehead using straps 2089. In particular configurations, as shown in the cross-sectional detail of FIG. 20B, the flexible hose 2010 can be surrounded with wire 2087 and wraps 2088 so that it can be bent to a shape that fits the face comfortably. These two FIGURES have been annotated with "Embodiment 5V," where "V," again stands for vent. Although Embodiment 5V is shown here, a similar Embodiment 5R (where "R," again stands for pressure "recovery") could be employed as well in this configuration.

Power Systems and Air Delivery/Retrieval

Figure 21:
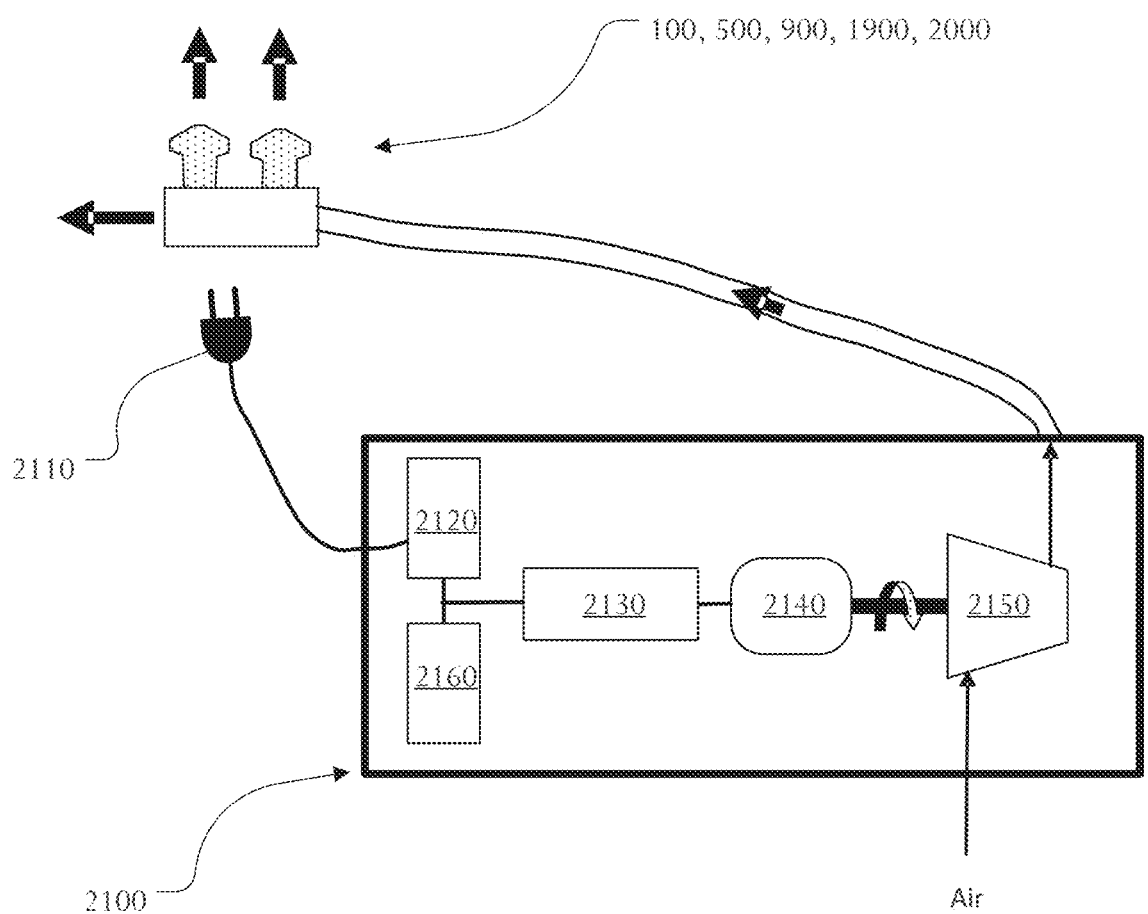
FIG. 21 shows the power system that produces compressed air for the vented air-delivery system embodiments of the disclosure.

FIG. 21 shows a power system 2100 that produces compressed air for the vented air-delivery systems (Embodiments 1V, 2V, 3V, 4V, and 5V—Embodiment 3V is shown as an example). Electrical energy is provided from a conventional electrical plug 2110 that receives energy from the electrical grid. A rectifier 2120 provides DC electricity to a controller 2130 that regulates the speed of a motor 2140. The motor 2140 powers the compressor 2150. In particular configuration, a battery 2160 can be incorporated into the electrical circuit to provide power in case the electrical grid fails or if the unit is to be used in remote locations (e.g., camping).

Figure 22:
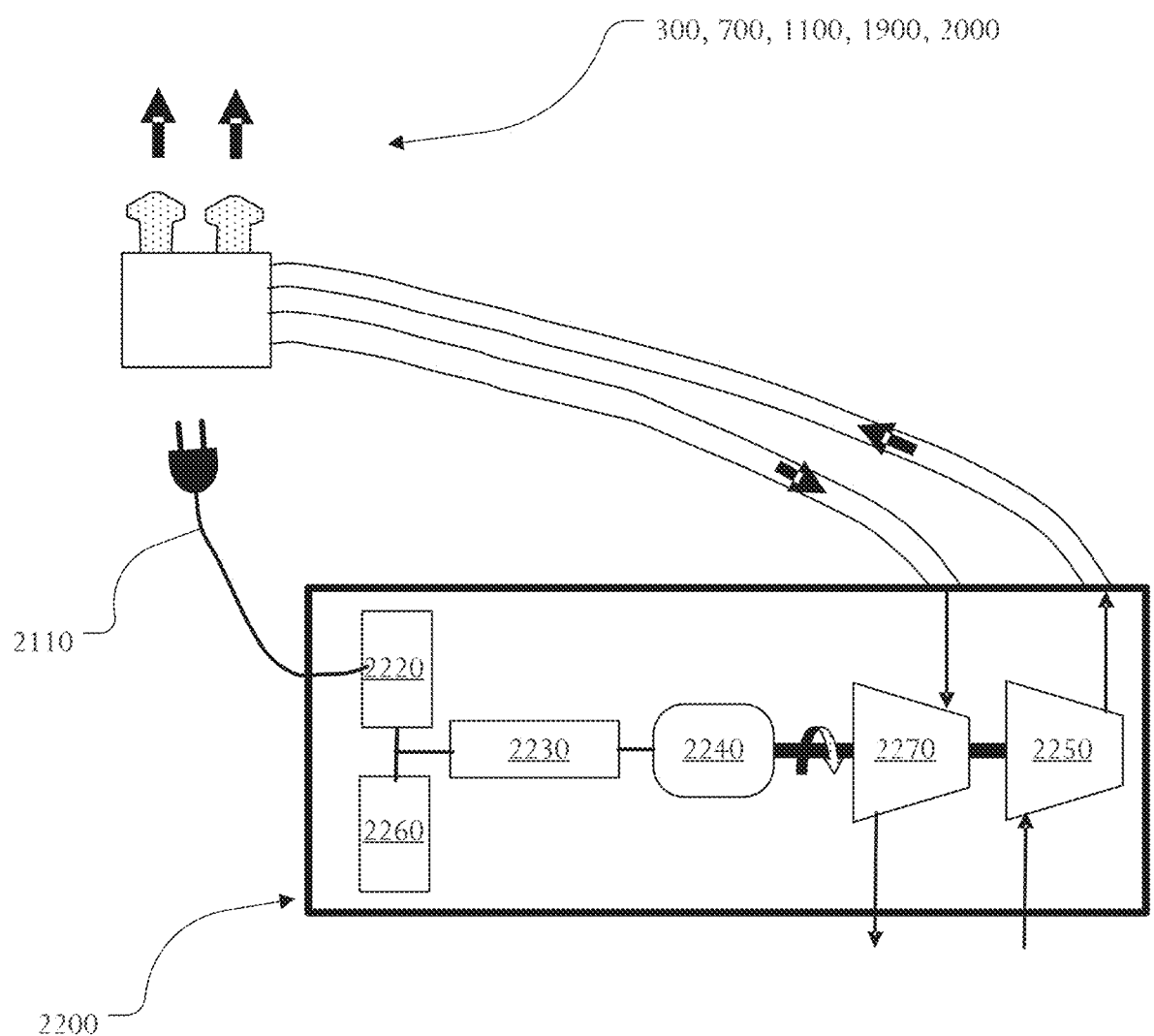
FIG. 22 shows the power system that produces compressed air for the pressure recovery air-delivery system embodiments of the disclosure.

FIG. 22 shows the power system that produces compressed air for the pressure recovery air-delivery systems (Embodiments 1R, 2R, 3R, 4R, and 5R—Embodiment 3R is shown as an example). It is nearly identical to FIG. 21 with electrical plug 2210, rectifier 2220, controller 2230, motor 2240, compressor 2250, and battery 2260; however, it also includes an expander 2270. The expander 2270 recovers shaft power from the vented high-pressure gas.

Cannula Seal Enhancements

Figure 23:
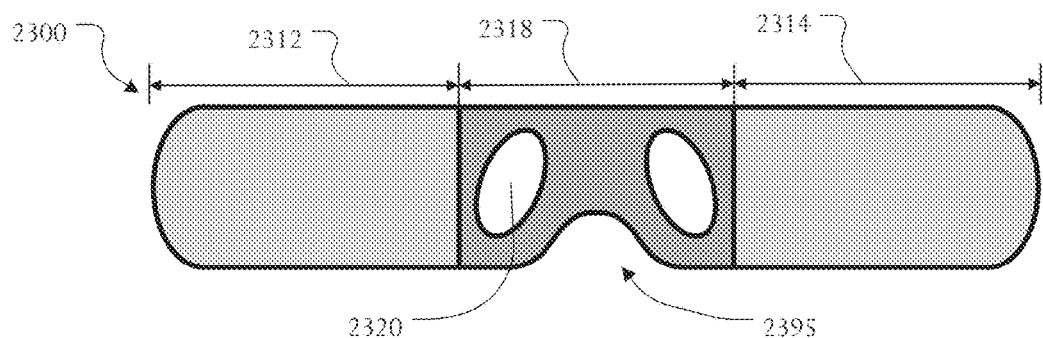
FIGS. 23, 24, and 25 show enhanced cannula-sealing apparatuses 2300 and 2400, according to additional embodiments of the disclosure.
Figure 24:
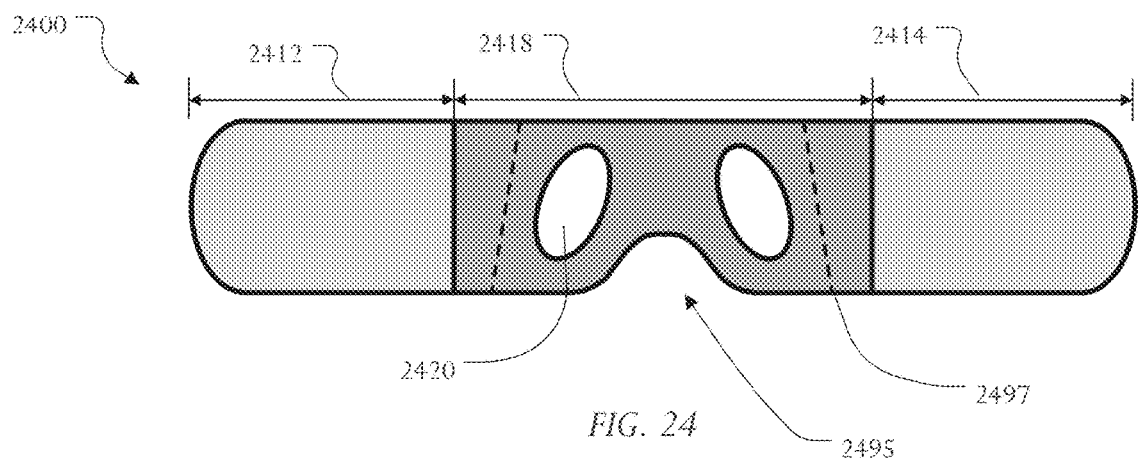
Figure 25:
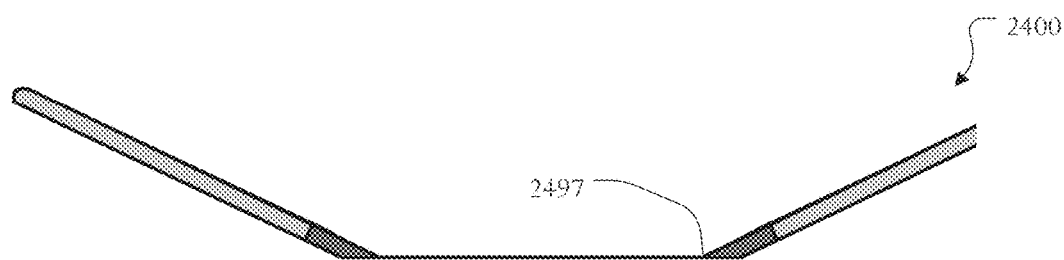

FIGS. 23, 24, and 25 show enhanced cannula-sealing apparatuses 2300 and 2400, according to additional embodiments of the disclosure. The cannula-sealing apparatuses 2300, 2400 of FIGS. 23, 24, and 25 may operate substantially in a similar manner to the cannula-sealing apparatus 1300 described with reference to FIGS. 13A, 13B, and 13C, including continuous member 1310 with two holes 1320 and portions 1312, 1314, and 1318. However, cannula-sealing apparatuses 2300 and 2400 of FIGS. 23, 24, and 25 also include notches 2395 and 2495 that accommodate the columella—the fleshy skin that separates the two nostrils. Additionally, cannula-sealing apparatuses 2400 of FIGS. 24 and 25 also includes a crease 2497 is that provides a fold that helps guide the installation.

It will be understood that well-known structural details have not been described in detail and have been omitted for brevity. Although specific structures and materials may have been described, the present disclosure may not be limited to these specifics, and others may be substituted as it is well understood by those skilled in the art.

What is claimed is:

1. A universal sealing apparatus comprising:
   a first portion configured to removably adhere directly or indirectly to a first outer side of a nose;
   a second portion configured to removably adhere directly or indirectly to a second outer side of the nose; and
   a third portion between and coupling the first and second portions, the third portion configured to:
     removably receive multiple cannulas of a pressurized air-delivery system that are configured to be inserted through the third portion of the universal sealing apparatus and into nostrils of the nose, the cannulas having flared portions, and
     place a force upon bases of the flared portions of the cannulas when the first and second portions are adhered to the nose to maintain the flared portions of the cannulas within the nostrils of the nose and to maintain fluid seals of the cannulas with the nose;
   wherein the third portion comprises:
     multiple holes, each hole configured to receive and allow passage of one of the cannulas completely through the third portion;
     a reinforcement located at least around the holes; and
     multiple creases that extend through the third portion including through the reinforcement of the third portion and that provide folding lines for the universal sealing apparatus, the holes positioned between the creases.

2. The apparatus of claim 1, wherein the holes are configured to:
   allow passage of the flared portions of the cannulas through the third portion when deformed; and
   restrict passage of the flared portions of the cannulas through the third portion when not deformed.

3. The apparatus of claim 1, wherein the third portion further comprises a notch configured to accommodate a columella of the nose.

4. The apparatus of claim 3, wherein the notch is positioned along a longer side of the apparatus, the notch located between the holes and between the creases.

5. The apparatus of claim 1, wherein the first and second portions include an adhesive that allows the first and second portions to directly adhere to the nose.

6. The apparatus of claim 5, wherein the adhesive is a pressure-sensitive adhesive configured to adhere to skin when pressed.

7. The apparatus of claim 1, wherein the first and second portions are removably coupleable to the third portion.

8. The apparatus of claim 7, wherein the first and second portions are configured to be disposed upon a loss of or reduction of an ability to adhere directly or indirectly to the nose without disposing of the third portion.

9. The apparatus of claim 1, wherein the apparatus is configured to be disposed upon a loss of or reduction of an ability of one or both of the first and second portions to adhere directly or indirectly to the nose.

10. The apparatus of claim 1, wherein the first, second, and third portions are continuous.

11. The apparatus of claim 1, wherein the first, second, and third portions are formed from a common material.

12. The apparatus of claim 1, wherein the third portion is configured to receive different cannulas from different cannula, nose pillow, or pressurized air-delivery system manufacturers.

13. The apparatus of claim 1, wherein the third portion extends past both of the creases.

14. A system comprising:
    a pressurized air-delivery system comprising multiple cannulas configured to be inserted into nostrils of a nose; and
    a universal sealing apparatus comprising:

a first portion configured to removably adhere directly or indirectly to a first outer side of the nose;

a second portion configured to removably adhere directly or indirectly to a second outer side of the nose; and a third portion between and coupling the first and second portions, the third portion configured to:

removably receive the cannulas of the pressurized air-delivery system, the cannulas configured to be inserted through the third portion of the universal sealing apparatus and into the nostrils of the nose, the cannulas having flared portions; and place a force upon bases of the flared portions of the cannulas when the first and second portions are adhered to the nose to maintain the flared portions of the cannulas within the nostrils of the nose and to maintain fluid seals of the cannulas with the nose;

wherein the third portion comprises:

multiple holes, each hole configured to receive and allow passage of one of the cannulas completely through the third portion;

a reinforcement located at least around the holes; and multiple creases that extend through the third portion including through the reinforcement of the third portion and that provide folding lines for the universal sealing apparatus, the holes positioned between the creases.

15. The system of claim 14, wherein the pressurized air-delivery system comprises a Continuous Positive Airway Pressure (CPAP) device.

16. The system of claim 14, wherein the first and second portions lack the reinforcement.

17. The system of claim 14, wherein the first and second portions are removably coupleable to the third portion.

18. A method comprising:

inserting multiple cannulas of a pressurized air-delivery system through a universal sealing apparatus, the cannulas having flared portions; and attaching the universal sealing apparatus to a nose in order to seal the cannulas within nostrils of the nose;

wherein the universal sealing apparatus comprises:

a first portion configured to removably adhere directly or indirectly to a first outer side of the nose;

a second portion configured to removably adhere directly or indirectly to a second outer side of the nose; and a third portion between and coupling the first and second portions, the third portion configured to:

removably receive the cannulas through the third portion; and place a force upon bases of the flared portions of the cannulas when the first and second portions are adhered to the nose to maintain the flared portions of the cannulas within the nostrils of the nose and to maintain fluid seals of the cannulas with the nose;

wherein the third portion comprises:

multiple holes, each hole configured to receive and allow passage of one of the cannulas completely through the third portion;

a reinforcement located at least around the holes; and multiple creases that extend through the third portion including through the reinforcement of the third portion and that provide folding lines for the universal sealing apparatus, the holes positioned between the creases.

19. The method of claim 18, wherein the third portion is configured to receive different cannulas from different cannula, nose pillow, or pressurized air-delivery system manufacturers.

20. The method of claim 18, wherein the first and second portions are removably coupleable to the third portion.

21. The method of claim 18, further comprising:

after the flared portions of the cannulas are inserted through the holes of the third portion and the first and second portions are adhered to the nose, delivering pressurized air through the cannulas to the nose while the fluid seals prevent air leakage from the nose.

\* \* \* \* \*